(12) United States Patent
McGinley et al.

(10) Patent No.: US 11,576,684 B2
(45) Date of Patent: Feb. 14, 2023

(54) DRILL BIT DATA MANAGEMENT FOR PENETRATION-MONITORING DRILL

(71) Applicant: McGinley Engineered Solutions, LLC, Casper, WY (US)

(72) Inventors: Joseph C. McGinley, Casper, WY (US); Adam M. Johnson, Casper, WY (US)

(73) Assignee: MCGINLEY ENGINEERED SOLUTIONS, LLC, Casper, WY (US)

( * ) Notice: Subject to any disclaimer, the term of this patent is extended or adjusted under 35 U.S.C. 154(b) by 378 days.

(21) Appl. No.: 16/765,560

(22) PCT Filed: Nov. 21, 2018

(86) PCT No.: PCT/US2018/062181
§ 371 (c)(1),
(2) Date: May 20, 2020

(87) PCT Pub. No.: WO2019/104121
PCT Pub. Date: May 31, 2019

(65) Prior Publication Data
US 2020/0305894 A1    Oct. 1, 2020

Related U.S. Application Data

(60) Provisional application No. 62/589,230, filed on Nov. 21, 2017.

(51) Int. Cl.
*A61B 17/16* (2006.01)
*A61B 90/98* (2016.01)
*A61B 90/00* (2016.01)
*A61B 17/00* (2006.01)

(52) U.S. Cl.
CPC .......... *A61B 17/1626* (2013.01); *A61B 90/98* (2016.02); *A61B 2017/00398* (2013.01); *A61B 2090/062* (2016.02); *A61B 2090/064* (2016.02)

(58) Field of Classification Search
CPC ................................................. A61B 17/1626
See application file for complete search history.

(56) References Cited

U.S. PATENT DOCUMENTS

| | | | |
|---|---|---|---|
| 5,833,704 A | 11/1998 | McCombs | |
| 6,665,948 B1 * | 12/2003 | Kozin | A61B 90/06 175/45 |
| 8,529,567 B2 * | 9/2013 | Garcia | A61B 17/16 606/104 |
| 2007/0085496 A1 | 4/2007 | Philipp | |

(Continued)

*Primary Examiner* — Christian A Sevilla
(74) *Attorney, Agent, or Firm* — Holzer Patel Drennan

(57) ABSTRACT

Embodiments directed to an apparatus and system of monitoring an instrument with a working tool engaged thereby. In one aspect, an embodiment including a working tool with a machine readable indicium indicative of a working tool attribute. The working tool may be receivable by an instrument such that a corresponding machine readable indicia reader receives an identifier of the working tool. Various attributes and conditions in relation to the instrument and working tool received thereby may be identified to facilitate the provisioning of a response to prompt various corrective actions. In this regard, a controller may provide an output in response to a received identifier of a working tool and an identified instrument operating condition.

17 Claims, 18 Drawing Sheets

(56) References Cited

U.S. PATENT DOCUMENTS

| | | |
|---|---|---|
| 2009/0292304 A1 | 11/2009 | Malackowski |
| 2013/0307529 A1 | 11/2013 | Baumgartner |
| 2015/0148805 A1 | 5/2015 | McGinley |
| 2015/0164436 A1 | 6/2015 | Maron et al. |
| 2015/0272608 A1* | 10/2015 | Gladstone .......... A61B 17/1626 606/167 |
| 2017/0128081 A1 | 5/2017 | McGinley |

* cited by examiner

BICORTICAL DRILL PATH

UNICORTICAL DRILL PATH

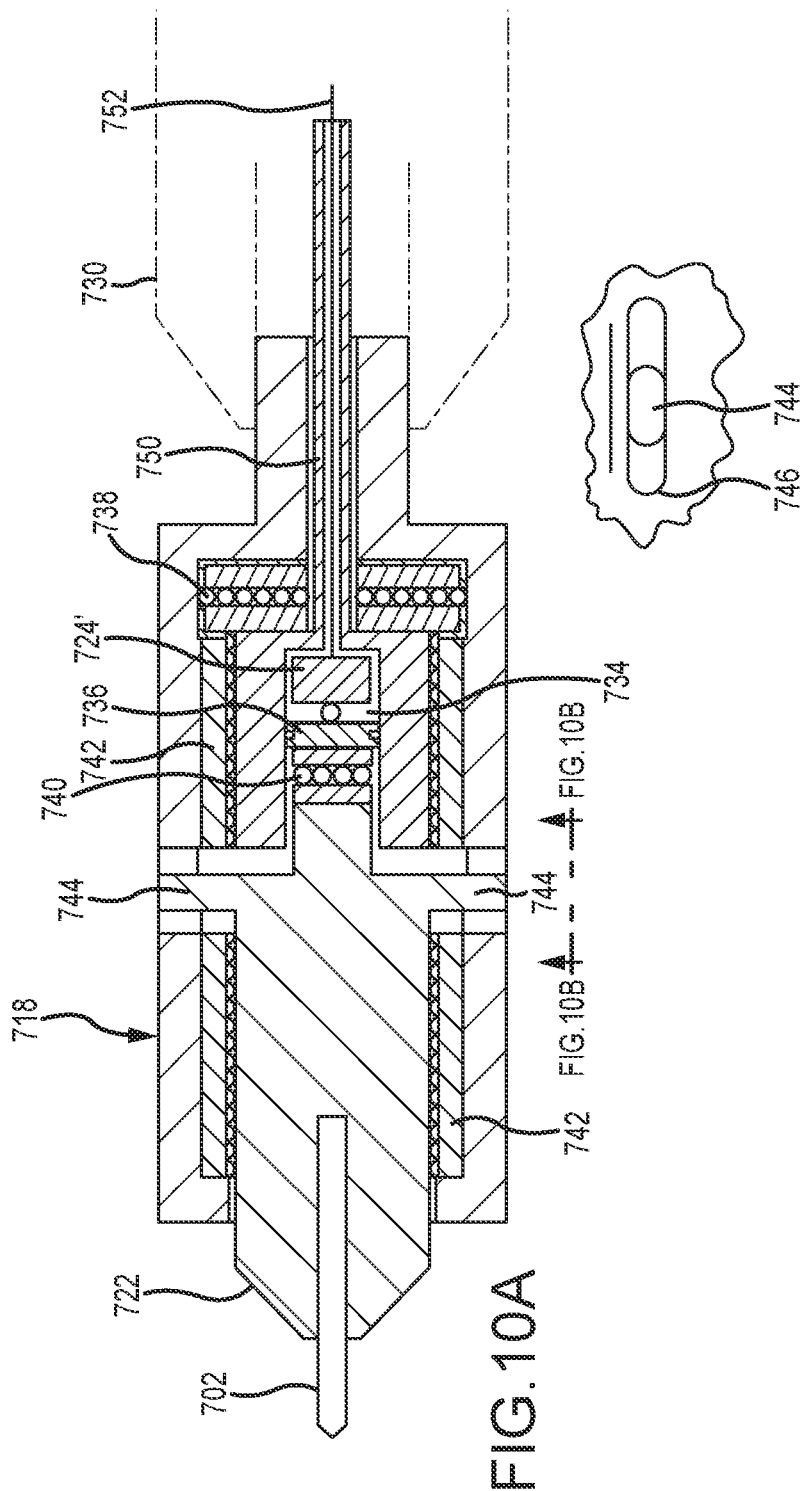

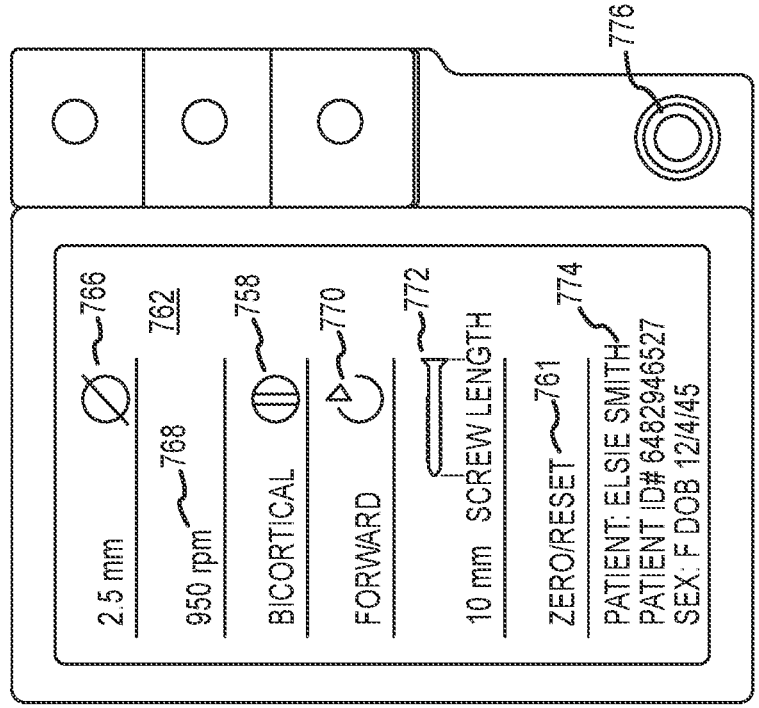
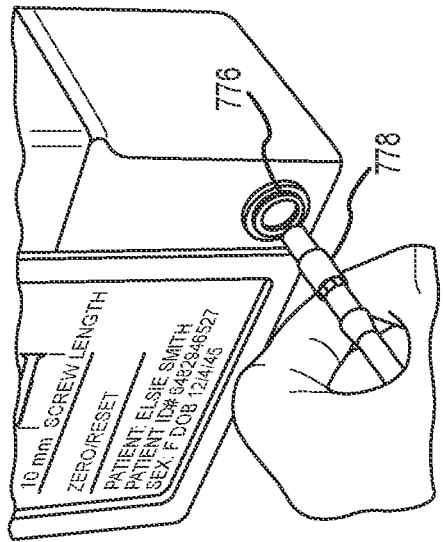
FIG. 15A
FIG. 15B

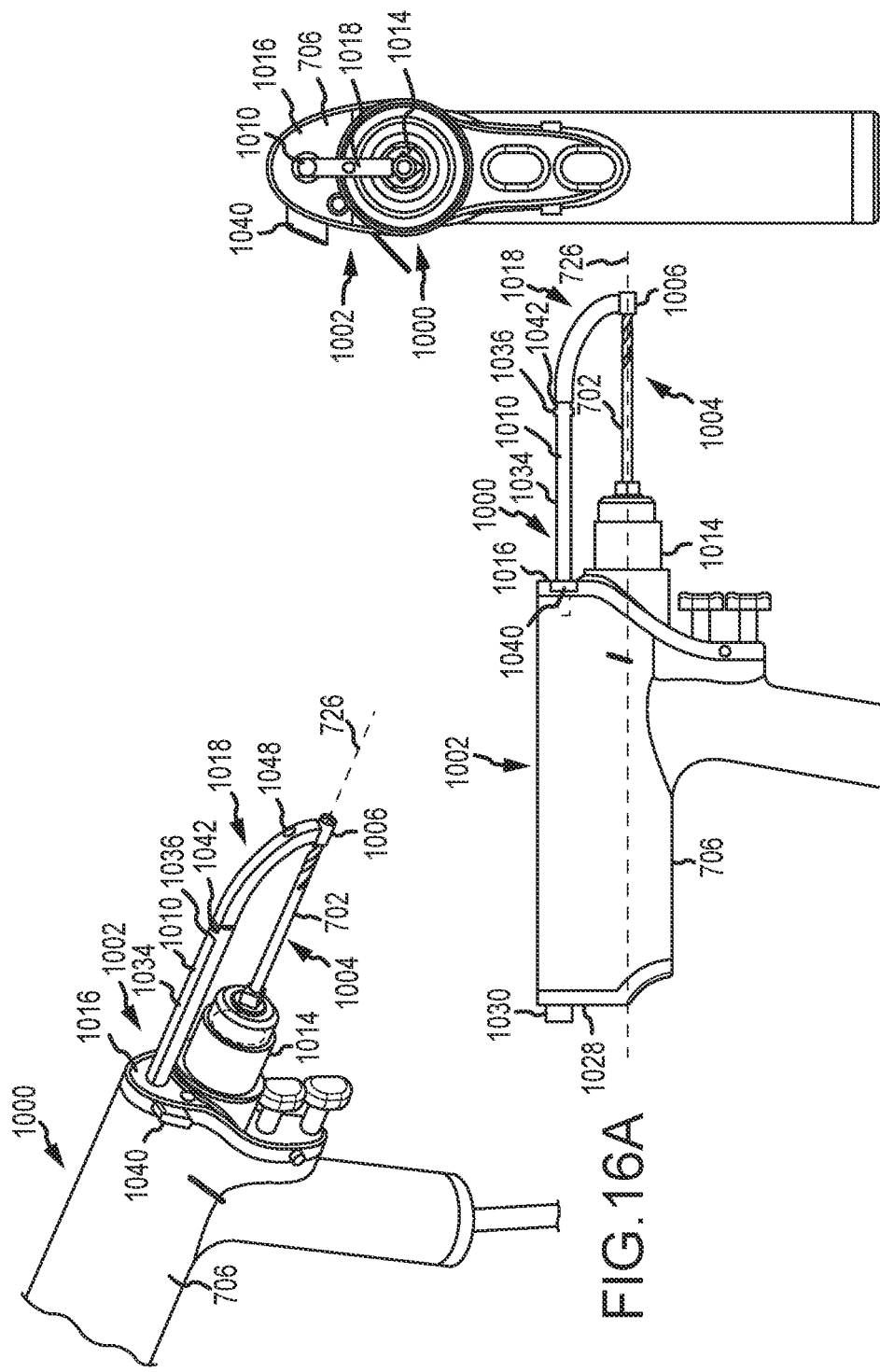

DRILL BIT DATA MANAGEMENT FOR PENETRATION-MONITORING DRILL

FIELD

The present invention generally relates to powered surgical instruments, and in particular to powered surgical instruments that releasably engage a working tool to perform an operation.

BACKGROUND

Various powered surgical instruments (e.g., drills, saws, grinders, etc.) may be associable with a plurality of corresponding working tools (e.g., drills bits, saw blades, grinding burrs, etc.) to facilitate certain operations using the powered surgical instruments. For example, a handheld drill may engage any one of a plurality of drill bits in order to bore a hole through a medium of interest such as an anatomical structure of a patient. Further, in such settings, each of the plurality of working tools may embody certain attributes including but not limited to a certain size, serial number, material composition, manufacturer, temperature tolerance, and the like. For example, a first respective drill bit may constitute a first bore diameter and a first material made by a first manufacturer, while a second respective drill bit may constitute a second bore diameter and a second material made by a second manufacturer. In this regard, the operation of the instrument including the functionality, specifications, and limitations related thereto may be at least partially based on the particular respective working tool engaged by the powered surgical instrument. That is, the specific attributes of the engaged working tool may at least partially inform or otherwise impact the functionality of the instrument, for example, by defining the operational limitations of the instrument in relation to the engaged working tool. In this regard, the first respective drill bit with the first bore diameter and first material may limit the rotational speed, for example, at which the instrument may be used to bore a hole, etc.

Further, some electro-mechanical instruments may include one or more sensors integrated therein to measure various conditions of the instrument and/or of the operational environment thereof such as the density of a medium through which a working tool is advanced during use. In this regard, in such circumstances, the values measured by the one or more sensors of the instrument and any outputs related thereto may be at least partially based on the particular engaged working tool and its associated attributes. As such, with regards to the foregoing, it may be desirable to identify the particular engaged working tool and the attributes related thereto.

SUMMARY

In view of the foregoing, the present disclosure facilitates a system for monitoring an instrument and a working tool engaged by the instrument. The instrument may be a powered surgical instrument and the working tool may be used in conjunction with the powered surgical instrument for performing an operation. The system may facilitate generation of an output or signal from an indicia reader responsive to detection of an indicium associated a working tool. An indicium may be indicative of or associated with a working tool attribute and/or instrument operating condition. The invention allows a user of the instrument to effectively manage a system in which a plurality of working tools may be engageable by the instrument so as to identify relevant information in relation to a respective working tool engaged by the instrument. The invention further allows the user to identify relevant information in relation to one or more measurable or determined conditions associated with the instrument that may prompt or otherwise facilitate corrective or other remedial action.

BRIEF DESCRIPTION OF THE DRAWINGS

FIG. 10A is an enlarged sectional view of an embodiment of the drill bit load measurement assembly of FIG. 7.

FIG. 10B is a sectional view of a portion of the drill bit load measurement assembly taken along the line 10b-10b of FIG. 10A.

FIGS. 15A and 15B depict an embodiment of a controller for use in operation of a drill having a drill bit penetration measurement system.

FIGS. 16A, 16B, and 16C are perspective, side, and front views, respectively, of an embodiment of a drill comprising a drill bit penetration measurement system.

DETAILED DESCRIPTION

Figure 1:
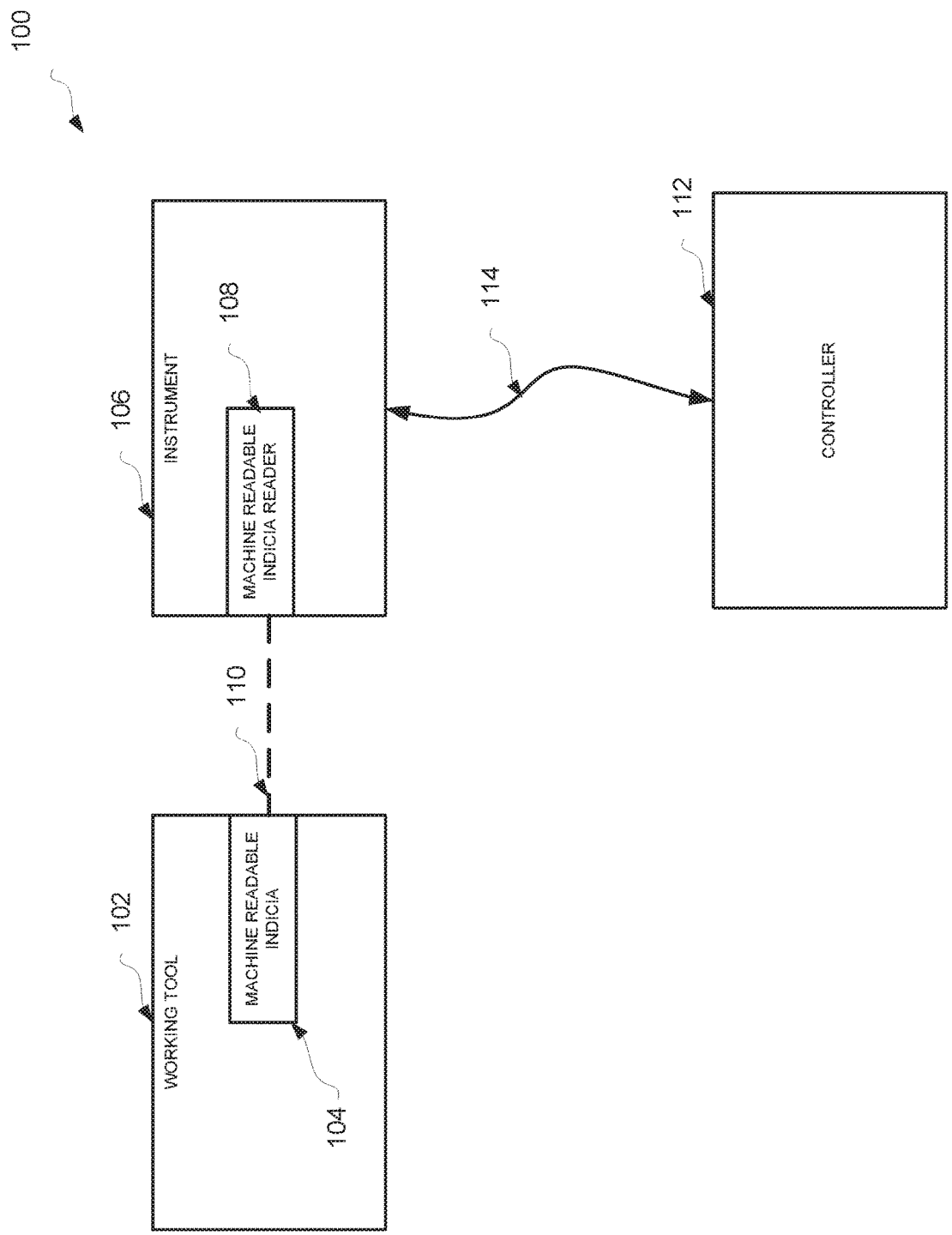
FIG. 1 depicts an embodiment of a monitoring system for monitoring an instrument and working tool engaged thereby.

Disclosed herein are utilities (e.g., systems, processes, etc.) for monitoring an instrument operatively associated with a working tool. In this regard, the disclosed utilities include a working tool having a machine readable indicium associated with at least one working tool attribute. The working tool may be receivable by the instrument, for example, via operation of a chuck or other receiving element operable to receive or otherwise secure and engage the working tool therein. Upon receipt of a working tool, a corresponding machine readable indicia reader may analyze the indicium to determine an identifier associated with the working tool. The identifier may be used to retrieve a working tool attribute from a database or may directly convey a working tool attribute. For example, in the former instance, the identifier may comprise a serial number which may be used to identify working tool attributes. In the latter instance, the identifier may directly indicate a working tool attribute such as a manufacturer thereof. The machine readable indicia reader may transmit an identifier, the same as or different than the identifier received at the machine readable indicia reader, to a controller for processing. The disclosed utilities may also include a displacement measuring apparatus (or other appropriate measuring apparatus) disposed in corresponding relation to the working tool to measure displacement of the working tool relative to an axis along which the working tool may be advanced during use. In some instances, additional or alternative measuring apparatuses may be provided, as discussed below. The disclosed utilities may also include a controller (mentioned above) in operative communication with the instrument and configured to provide an output responsive to a working tool attribute received, for example, from a database. The output may be displayed to a user on a display monitor or may be transmitted to the instrument to influence the operation thereof.

Working tool attributes may be utilized in many respects. In some cases, a working tool attribute may be used to maintain an inventory of working tools. For example, a current inventory present at a hospital or other site may be automatically maintained wherein a quantity is reduced upon the reading of an indicium associated with a particular type of working tool represented by the quantity. As another example, each working tool used during an operation may be entered into a list such that upon completion of the operation, personnel may take inventory of working tools brought into the operating room to verify that all working tools are accounted for.

Additionally, working tool attributes may be monitored to ensure safe operation of an instrument. For example, a particular instrument may be prevented from operating unless and until one or more attributes of a working tool associated therewith have been verified as compliant with required specifications. As another example, an instrument may be disabled upon a determination, based upon an indicium associated with the working tool, that the working tool is not new from the factory but rather has been used with another patient or has been refurbished by an unlicensed party.

Finally, working tool attributes may be recorded in a database of surgical operation statistics to improve medical procedures. For example, during an operation, a drill may record operating conditions such as force applied, motor speed, and displacement into a patient's bone. This information may be recorded in conjunction with demographics about the patient and attributes associated with the drill bit utilized. In this regard, determinations may be made regarding optimal drill bit size, materials, and methods of use.

Certain terminology is used in the following description for convenience only and should not be considered as limiting. The words "inwardly" and "outwardly" refer to directions toward and away from, respectively, the geometric center of the systems and designated parts thereof described herein. The terminology includes the words above specifically mentioned, derivatives thereof and words of similar import.

Additionally, as used in the claims and in the corresponding portion of the specification, the word "a" means "at least one," the word "about" when used in conjunction with a numerical value means a range of values corresponding to the numerical value plus or minus ten percent of the numerical value, and the word "or" has the meaning of a Boolean inclusive "Or." For example, the phrase "A or B" means "A" alone or "B" alone or both "A" and "B."

As used herein, the term "instrument" may refer to any tool or device, powered or manually operated, which is configured for use with a removable and replaceable part referred to herein as a working tool. For example, an instrument may be a drill, a saw, a screwdriver, etc. and a working tool may be a drill bit, a saw blade, a screwdriver bit, etc. A machine readable indicium may be any device or marking that is capable of being read, interpreted, analyzed, or otherwise received by a machine. For example, a machine readable indicium may be a radio frequency identification (RFID) tag, a bi-directional sensor, a barcode, a QR code, an alphanumeric identifier, etc. Notably, a machine readable indicium need not be readable by machine only but may also be readable by a user. A machine readable indicia reader may be any device configured to observe, scan, read, or otherwise detect a machine readable indicium. For example, a machine readable indicia reader may be an RFID reader, an optical sensor, a laser scanner, camera, etc.

Machine readable indicia may be configured to convey a working tool attribute directly or may convey an identifier which can be used to look-up working tool attributes from a database stored locally or remotely. For example, a machine readable indicium may convey an identifier such as a serial number to the machine readable indicia reader. The machine readable indicia reader, or a device in operative communication therewith such as a controller, may then reference a database to retrieve working tool attributes associated with the serial number. Notably, "working tool attributes" as that term is used herein in reference to information received at a controller or instrument from a database may refer to working tool attributes themselves or may refer indications of working tool attributes. To illustrate, a database may convey to a controller that a particular identifier sent from the controller to the database is associated with a size "3" drill bit. The numerical value "3" may then be conveyed to the controller which references a data repository to determine that a size "3" drill bit is 4 inches long and has a ⅛" diameter. In this regard, "3" may be considered an indication of a working tool attribute rather than a working tool attribute itself. Working tool attributes may include a working tool size, a working tool serial number or other identifier, a material from which the working tool is constructed, a manufacturer of the working tool, any prior uses of the working tool, an optimum, maximum, or minimum instrument operating speed associated with the working tool, or any other relevant information concerning the working tool.

The term "identifier" as used herein may refer to any information which is conveyed by an indicium and useful for determining a working tool attribute. In some instances, an identifier may itself be, or may directly convey, a working tool attribute and in other instances, an identifier may be an alphanumeric sequence with working tool attributes encoded therein. A controller may decipher the identifier to determine the working tool attributes.

A controller, as that term is used herein, may be any device having or associated with a processing engine which is operable to monitor an instrument, display properties associated with the instrument, and/or control operation aspects of the instrument. In some instances, a controller may be integrated directly into an instrument, it may be disposed adjacent an instrument and in operative communication therewith, or may be disposed remotely and configured for communication with the instrument via a wired or wireless network. A controller may be operable to receive an identifier from a machine readable indicia reader and reference a local or remote database to retrieve working tool attributes associated with the identifier. In response to receiving certain working tool attributes, a controller may be configured to allow an instrument to operate using the respective working tool or may prevent the instrument from operating. For example, if a working tool attribute indicates that a working tool has previously been used with another patient, a controller may prevent a drive motor of the instrument from receiving control signals, thereby disabling the instrument. A default status of a drive motor may be set by a controller to "operative" such that the instrument will work unless and until a working tool attribute is determined to be unacceptable. Alternatively, a default status of a drive motor may be set by a controller to "inoperative" such that the instrument will not work unless and until all working tool attributes considered critical are determined to be acceptable. The determination of whether a working tool attribute is acceptable or unacceptable may be executed using a series of rules (discussed below).

Broadly, the disclosed embodiments relate to monitoring an instrument that is operatively associable with any one of a plurality of working tools. This may be desirable, for example, in environments in which each of a plurality of working tools exhibits different attributes which, in turn, influence the operation or use of the instrument. In this regard, the operative association of one of the plurality of working tools with the instrument may facilitate reading an indicium disposed at the working tool and associated with or directly communicating one of the particular attributes of the working tool. In this regard, the invention may be used for identifying a working tool attribute of interest of a received working tool so that a controller may provide an output responsive to the identified working tool attribute of interest. Such an output may be a signal to enable or disable the instrument or a component thereof, may be a signal to trigger an alarm or alert to the user, for example, indicating that the working tool may be undesirable for the instant operation, or may affect an operating condition of the instrument. For example, a working tool attribute indicating a maximum drive speed of 100 RPM may result in the controller outputting a signal that limits the drive motor in the instrument to 100 RPM. A working tool attribute may be received or selected at a controller by referencing a database using the identifier transmitted by the machine readable indicia reader. For example, the machine readable indicium may be disposed in proximal relation to the machine readable indicia reader such that the machine readable indicia reader transmits an identifier corresponding to the indicium. In this regard, as each working tool may include a respective machine readable indicium, the controller may provide an output responsive to characteristics or properties of the respective working tool received at the instrument.

In certain other embodiments, described below, the disclosed utilities also include a data collection module operatively associated with a displacement measuring apparatus for identifying an instrument operating condition. "Instrument operating condition" may refer to a condition corresponding to the operation of the instrument itself, the operating environment of the instrument, and/or any other conditions or parameters of interest that may facilitate monitoring an instrument, according to the embodiments described herein. For example, the data collection module may include or utilize a processor for identifying an instrument operating condition at least partially based on a measured displacement of the working tool. For example, the present invention may determine a condition corresponding to the operating condition of the instrument, such as the density of an environment through which the working tool is advanced during use. Such a determination may be made based upon a measured force applied to the working tool, the displacement of the working tool, and working tool attributes.

In other embodiments, a processor may identify an instrument operating condition at least partially based on a working tool attribute received by the instrument or controller. For example, by receiving a known weight of the working tool, the processor may be able to determine a magnitude of torque being applied to the working tool by the instrument.

In some instances, the instrument operating condition may facilitate monitoring an inventory level of working tools that are associable with the instrument. This may occur, for example, by counting the instances of a working tool attribute received which correspond to unique working tools over a period of time and correlating the received working tool attributes to determine an inventory level. For example, a database may be used to store a dynamic count of each time a working tool is used having a particular attribute, such as a ⅜" diameter. In this regard, the count may be increased by manual or automatic entry of a quantity of working tools received in a delivery and may be decreased by one each time a uniquely identified working tool having the attribute of interest is used.

It should be appreciated, however, that alternative or additional measuring apparatus embodiments may be utilized in accordance with the present invention, which may be used to identify the instrument operating condition or provide other information of interest. For example, in addition or in the alternative to the disclosed displacement measuring apparatus, the instrument may include a rotational measuring apparatus disposed in corresponding relation to the working tool to measure rotational characteristics of the instrument such as angular velocity, angular frequency, torque, etc. A processor may obtain measured rotational characteristics of the instrument for identifying an instrument operating condition. As another example, the instrument may include a power systems measuring apparatus disposed in corresponding relation to a drive mechanism of the instrument to measure characteristics in relation to the operation of the working tool such as voltage and current fluctuations, powers, resistance, efficiency, run-time limitations, such as overheating, etc. A processor may obtain the measured characteristics of the instrument for identifying an instrument operating condition. In yet other embodiments, other measuring apparatuses are contemplated for measuring one or more characteristics of the instrument to facilitate the functionality of the disclosed monitoring system. Accordingly, the description below should be understood as exemplifying particular embodiments and implementations of the invention, and not by way of limitation.

Reference will be now be made to the accompanying drawings, which assist in illustrating the various pertinent features of the various novel aspects of the present disclosure. The following description is presented for purposes of illustration and description. Furthermore, the description is not intended to limit the inventive aspects to the forms disclosed herein. Consequently, variations and modifications commensurate with the following teachings, and skill and knowledge of the relevant art, are within the scope of the present inventive aspects.

In this regard, FIG. 1 presents a schematic representation an embodiment of a system 100 for monitoring an instrument that may include a working tool 102 with a machine readable indicium 104. In this regard, the machine readable indicium 104 may be indicative of a working tool attribute corresponding to the working tool 102. For example, the machine readable indicium 104 may be indicative of one or more working tool attributes of the working tool 102. In some instances, a machine readable indicium 104 may convey a first attribute such as an identifier which may be used to identify or retrieve additional attributes.

According to another embodiment, the system 100 may include a plurality of working tools 102 each with a respective machine readable indicium 104. In turn, the respective machine readable indicium 104 may be indicative of or associated with a working tool attribute corresponding to the respective working tool 102 with which the respective machine readable indicium 104 is associated. Accordingly, based in part on the machine readable indicium 104 facilitating the identification of a working tool attribute, the various characteristics or properties of the working tool may be communicated to an instrument or other associated hardware to, for example, identify the working tool 102 and facilitate the provision of an output responsive to a working tool attribute received in relation to the machine readable indicium 104.

The system 100 for monitoring an instrument may also include an instrument 106 with a machine readable indicia reader 108. In this regard, the machine readable indicia reader 108 may receive an identifier associated with working tool 102 via machine readable indicium 104. For example, working tool 102 may be received by the instrument 106 such that the machine readable indicia reader 108 receives an identifier associated with the working tool via the operative association of the machine readable indicia reader 108 with the machine readable indicium 104.

The machine readable indicium 104 may be disposed in proximal relation to the machine readable indicia reader 108 such that machine readable indicia reader 108 receives the identifier of the working tool via signal 110. In this regard, signal 110 may be an electromagnetic signal generated at the machine readable indicium 104 in part by an induced magnetic field at the machine readable indicia reader 108 (as may be the case for a passive RFID tag transferring electronically stored information to an RFID reader that produces a magnetic field). In other cases, signal 110 may include an optical signal for registration by the machine readable indicia reader 108.

Accordingly, based on the received identifier of the working tool, the instrument 106 may identify a particular received working tool 102 along with the characteristics or properties related thereto. That is, the system 100 may include a plurality of working tools 102, with each working tool 102 including a respective machine readable indicium 104 indicative of one or more working tool attributes associated with the respective working tool 102 at which the machine readable indicium is disposed. The instrument 106 may be associable with any of the plurality of working tools 102. In this regard, the instrument 106 may identify or otherwise register the particular working tool attributes associated with the respective engaged working tool 102 upon receipt of the working tool 102 at the instrument 106. The identification of the particular working tool attributes of the working tool 102 at the instrument 106 may be processed at the instrument 106 and/or transmitted from the instrument 106 to facilitate the provision of an output responsive to the received identifier and/or identification of the instrument operating condition.

The system 100 for monitoring an instrument may also include a controller 112 in operative communication with the instrument 106 via electronic signal 114. In this regard, the controller 112 may provide an output responsive to the received identifier. For example, the instrument 106 may include an antenna and/or other output device for transmission of electronic signal 114 to controller 112 such that controller 112 may provide an output based at least in part on the information received via the electronic signal 114. As such, the electronic signal 114 may carry or otherwise convey information associated with the working tool attribute and/or other characteristics, parameters, or conditions associated with the instrument 106 such that the controller 112 may provide an appropriate corresponding output. The output may be communicated, for example, via a user portal, local display, and/or other output element to facilitate monitoring the instrument 106 and corresponding working tool 102. Preferably, such communications of the electronic signal 114 are wireless. In this regard, the instrument 106 and controller 112 may each include an RF transceiver for conducting wireless communications in accordance with a public or proprietary protocol such as a WAN, a LAN, and/or the internet. The electronic signal 114 may also be communicated between the instrument 106 and the controller 112 via a wireline connection. In some embodiments, a controller may be at least partially disposed within a housing of an instrument and the electronic signal 114 may accordingly be contained within the instrument.

In this regard, the controller 112 may facilitate monitoring the instrument 106 by providing an output responsive to an identified instrument operating condition, discussed in greater detail below. That is, the controller 112 may provide any appropriate output to prompt, for example, corrective or other responsive actions by a user of the system 100. For example, the controller 112 may provide an output responsive to a received working tool attribute that indicates an inventory level corresponding to a plurality of working tools 102, which may prompt a user to take a corrective action in relation to the indicated inventory level such as ordering additional units. As another non-limiting example, the controller 112 may provide an output responsive to a received or determined instrument operating condition that indicates one or more characteristics corresponding to the environment in which the received working tool 102 advances during use.

Figure 2:
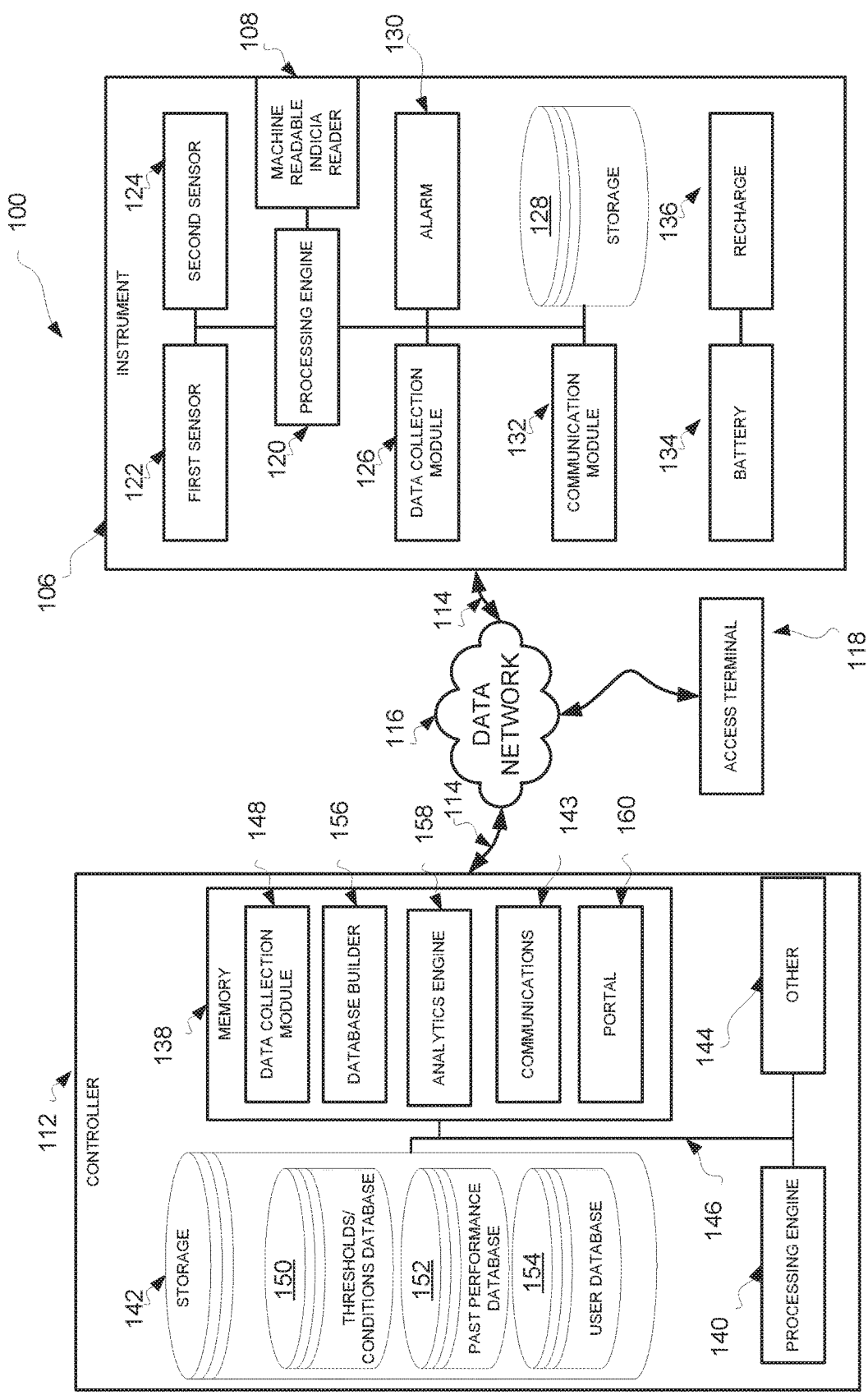
FIG. 2 is a functional block diagram of a controller and instrument for use in a system for monitoring an instrument, according to one embodiment.

In certain other embodiments, the controller 112 may be in operative communication with a remote server (not pictured) to facilitate analysis of the information received via electronic signal 114 in relation to one or more correlation factors determined at the remote server. For example, the correlation factors may be determined at the remote server based on communications received from a plurality of controllers. Notably, each of the plurality of controllers may be in operative communication with a respective instrument (or a plurality of instruments) and configured to collect data in relation to one or more parameters of the respective instrument or environment related thereto. In turn, this collected data may be transmitted to the remote server for determination of a correlation factor for application in subsequent utilizations of the instrument 106. In this regard, the controller 112 may provide an output responsive to a received identifier and/or identified instrument operating condition with respect to an instrument correlation factor determined at the remote server. The correlation factor may represent a threshold factor with which a measured value of the instrument 106 is compared to facilitate the identification of the instrument operating condition, etc. Turning next to FIG. 2, a detailed functional block diagram of system 100 is depicted in which various data attributes such as working tool attributes, instrument operating conditions, sensor values, and the like may be transmitted between the instrument 106 and the controller 112 to facilitate monitoring the instrument 106 and the working tool 102 received thereby. Broadly, the system 100 and the various components therein may include any appropriate hardware (e.g., computing devices, data centers, switches, antennas, etc.), software (e.g., logic, computer readable instructions, applications system programs, engines, etc.), network components (e.g., communication path interfaces, routers, etc.), and the like (not necessarily shown in the interest of clarity) for use in facilitating any appropriate operations of the network.

According to one embodiment, controller 112 and instrument 106 are configured for operative communication via electronic signal 114. Electronic signal 114 may be wired, wireless, or may be integrated into an instrument. Electronic signal 114 may be transmitted over one or more optional data networks 116 in order to support the disclosed monitoring of instrument 106. In this regard, the controller 112 may be provided locally to generate a response to facilitate real-time corrective actions, such as when indicating an environmental condition through which a received working tool 102 is advanced during use or may be provided remotely to generate a response to facilitate system remediation, such as when indicating an inventory level of a plurality of working tools 102 that are associable with the instrument 106, etc. In some instances, an access terminal 118 may be provided for bi-direction communication with the instrument 106 and the controller 112 via the one or more data networks 116. The access terminal 118, discussed in greater detail below, may facilitate providing the output responsive to the received identifier and/or the instrument operating condition by presenting the provided output of the controller as a visual or interactive display, etc.

The instrument 106 may generally employ various components to receive an identifier of a working tool and facilitate the provisioning of an output responsive to the received identifier. The instrument 106 may also include various components to identify an instrument operating condition and facilitate the provisioning of an output related thereto. In this regard, the instrument 106 may include machine readable indicia reader 108 operatively connected to and controlled by processing engine 120. Processing engine 120 may be integrally included with instrument 106 to execute various modules or engines of the instrument 106, including facilitating the operation of various associated sensors or other data collection and analysis devices.

The instrument 106 may include one or more modules designed to collect and/or process information to facilitate the provision of a responsive output at the instrument 106, controller 112, or other connected output device. As such, in the illustrated embodiment, the instrument 106 may include a first sensor 122 and a second sensor 124 configured to measure one or more parameters of interest. In this regard, the first and second sensors 122, 124 may be embodied as a measuring apparatus for identifying one or more characteristics of the instrument 106. For example, the first or second sensor 122, 124 may correspond to a sensor for use in a displacement measuring apparatus. In other embodiments, the first or second sensor 122, 124 may correspond to a sensor for measuring the rotational characteristics of the received working tool 102, a sensor for measuring the power characteristics of the instrument 106 such as voltage and current fluctuations, power efficiency, etc. or any other sensor for measuring a parameter of interest such as a force sensor configured to monitor an amount of force exerted by a user to advance an instrument. In this regard, an output from the first and second sensors 122, 124 may be provided to the processing engine 120 as an electronic signal for manipulation, processing, and/or transmitting according to the embodiments described below.

For example, the instrument 106 may also include data collection module 126 operatively associated with the processing engine 120 and first and second sensors 122, 124 for identifying an instrument operating condition. In this regard, data collection module 126 may obtain data collected at first and second sensors 122, 124 via processing engine 120 to identify the instrument operating condition.

Various parameter values or combinations of parameter values may be utilized to identify the instrument operating condition—the precise value, however, may vary depending on various factors, including the particular received working tool 102, the environment of the instrument 106, and/or the instant operation or application, as may be specified or preprogrammed by a user of the system 100. In one embodiment, in which first sensor 122 includes a sensor for use in a displacement measuring apparatus, information associated with the force applied at the working tool 102, information associated with the displacement of working tool 102 (i.e., relative to an axis along which the working tool 102 is advanced during use), and/or derivatives thereof may be utilized to identify an instrument operating condition indicative of, for example, a density of a material through which the working tool is advanced during use. In some instances, it may be desirable to process the identified instrument threshold values or algorithms such that the instrument 106 may provide an output that prompts a user to take one or more corrective actions.

In relation to the above instrument operating condition indicative of density, for example, it may be desirable to generate an alarm via actuation of alarm module 130 (discussed in greater detail below) if the instrument 106 attempts to advance a working tool 102 through an environment consisting of a density that exceeds a predetermined value, such as 5.00 or 5.50 g/cm$^2$. Alternatively, an alarm may be generated based on an abrupt increase or decrease in density such as more than 0.5 g/cm$^2$ in one second or several seconds, for example. As another alternative, an alarm may be generated based on a combination of these parameters such as density is rising at more than 0.5 g/cm$^2$ per second and density exceeds 5.00 g/cm$^2$. It will be appreciated that such thresholds or related algorithms may be based on the particular application of the instrument 106, and may incorporate the various expertise, experience, and evolving standards of a user of system 100. It will be appreciated that additional or alternative instrument operating conditions along with associated threshold values and corresponding alarms may be determined at least partially analogous to the manner described above, including instrument operating conditions determined based on information received from other described embodiments of first and second sensors 122, 124 and information in relation to a received identifier.

To facilitate the foregoing generation of an alarm or other responsive output, various parameter values may be utilized, for example, to quantify a threshold condition, range, etc. In this regard, the foregoing parameter values may be stored in a local database in the instrument 106 such as storage 128. The storage 128 may include information for use by the processing engine 120 and data collection module 126 in executing the noted functionality. For example, the storage 128 may include standardized operating parameters or other attributes in relation to the instrument 106 and/or the received working tool 102, threshold values or algorithms to facilitate determination of alarm conditions, environmental conditions, and any other appropriate data attributes for determining when an alarm should be triggered. This information may be stored prior to use of the instrument 106 or may be updated via wireless or other methods via electronic signal 114, for example, transmitted over the one or more data networks 116.

The processing engine 120 may implement a variety of different algorithms for obtaining values such as those measured by first or second sensor 122, 124, identifying an instrument operating condition, and/or determining whether an alarm should be triggered. Such algorithms may involve simple comparison of values, such as comparing a current displacement value to a displacement value threshold. Alternatively, such algorithms may involve accessing one or more parameters from a remote server in order to facilitate the analysis of the obtained measured values, as discussed in greater detail below. For example, the processing engine 120 may determine a threshold displacement value appropriate for the instant operating conditions of the instrument 106 in part by reference to a remote central processor that provides a correlation factor based in part on aggregated information received from a plurality of instruments.

The alarm module 130 of instrument 106 may include an audio alarm, vibrating devices, wireless alerts, updated or other notifications via phone applications, a visual alarm, or any other system for alerting a user to the identified instrument operating condition. For example, the alarm module 130 may include LEDs, audio tone generators, or the like. In the case of the instrument 106 embodied as a handheld tool, visual alarms such as illuminating an LED when a threshold condition is reached may be particularly useful in notifying a user of an instrument operating condition. Accordingly, the alarm module 130, through one of the foregoing described techniques, may alert a user to the identification of an instrument operating condition or other determined output. In this regard, as the user is alerted to the instrument operating condition, the user may take appropriate corrective actions or be prompted by a third party to do so. For example, an alarm indicative of a target displacement of the working tool 102 may prompt the user to stop advancement of the working tool 102.

The instrument 106 may also include communication module 132 to facilitate the bidirectional communication between the instrument 106 and controller 112. For example, the communication module 132 may include an RF transceiver for conducting wireless communications. In other instances, the communication module 132 may include a port or other hardwired connection to facilitate wireline communications. In either event, the communication module 132 is configured to transmit and receive electronic signal 114 via the one or more data networks 116.

In some embodiments, the instrument 106 may also include a battery 134 operable for providing power to the instrument 106 and each of the associated processors, modules, and sensors included therein. In some instances, the battery 134 may be recharged by a recharge module 136, which may include a re-charge induction coil and/or a port for connecting to an AC power source or other recharging power source.

As described above, the instrument 106 may transmit one or more electronic signals to the controller 112 to facilitate the described monitoring of instrument 106 and received working tool 102. Accordingly, the controller 112 may include various components and modules to receive and transmit data with the instrument 106 to facilitate the foregoing functionality. In the illustrated embodiment, as depicted in FIG. 2, the controller 112 may include a memory 138 (e.g., RAM, other volatile modules, etc.) that contains one or more modules or engines that process data received from the one or more data networks 116; a processing engine 140 that executes the modules or engines from the memory 138; storage 142 (e.g., one or more magnetic disks, solid-state drives, or other non-volatile memory modules) for storing received and generated data; communications module 143; and a number of other components 144 (e.g., input devices such as a keyboard and a mouse, a transceiver in operative communication with the communications module 143 for transmitting and receiving electronic signals to and from the instrument 106, other devices such as a display and speakers, and the like), all of which may be appropriately interconnected by one or more system buses 146.

The one or more engines of the controller 112 may generally facilitate processing of data received via the one or more data networks 116 for monitoring of the instrument 106 and storing the resultant data in one or more databases of storage 142. Each of the engines may be in the form of one or more sets of computer readable instructions for execution by the processing engine 140, and may be manipulated by a user in any appropriate manner to analyze and configure the measured, received, or generated data as disclosed herein. Each of the engines may also be manipulated to configure the data stored in the one or more databases of storage 142 for transmission via the one or more data networks 116. In this regard, the combination of processing engine 140, memory 138, and/or storage 142, and the various engine/modules disclosed herein in one embodiment create a new machine that becomes a special purpose computer once it is programmed to perform particular functions of the utilities disclosed herein. While various engines have been depicted in FIG. 2 as being separate and distinct engines, it is understood that the functionalities or instructions of two or more engines may actually be integrated as part of the same computer-readable instruction set, and that the various engines have been depicted in the manner shown in FIG. 2 merely to highlight various functionalities of the system.

In one arrangement, the controller 112 may include a data collection module 148 that receives incoming data over the one or more data networks 116 for executing one or more processing functions and storing the received and/or processed data in storage 142 in any appropriate manner. In this regard, storage 142 may include a thresholds/conditions database 150 for storing various parameter values for use in identifying the instrument operating condition, etc.; a past performance database 152 for storing historical data and metrics associated with previously identified instrument operating conditions, including past and current inventory levels of a plurality of working tools 102 associable with the instrument 106, etc.; and a user database 154 for storing data associated with various users of the instrument 106, etc. In this regard, the controller 112 may also include a database builder 156 that is configured to manipulate the received and/or processed data to create, structure, or otherwise format the various databases of storage 142. In this regard, the database builder 156 may be configured to structure the various data attributes stored in storage 142 to facilitate the monitoring of instrument 106 and identification of an instrument operating condition. In this regard, the database builder may structure received data attributes of the thresholds/conditions database 150 in corresponding relation to various anticipated measured data attributes to facilitate identification of a corresponding instrument operating condition, etc.

As discussed above, controller 112 may include data collection module 148. According to one embodiment, data collection module 148 may perform substantially all of the functions described with respect to data collection module 126 of instrument 106, including the generation of an alarm output in relation to an identified instrument operating condition. In this regard, the data collection module 148 may be configured for identifying an instrument operating condition based on, for example, a measured data value obtained via the first or second sensors 122, 124. Additionally, the data collection module 148 may be configured for receiving an identifier of a working tool. In this regard, the data collection module 148 may receive data measured or generated at the instrument 106 for identifying the instrument operating condition and/or a working tool attribute.

The data collection module 148 may facilitate the identification of any instrument operating condition of interest as may be specified or otherwise preprogrammed, for example, by a user in relation to a particular use case, etc. In some instances, the identification of an instrument operating condition may involve accessing one or more databases of storage 142 for comparison or analysis with one or more measured or generated data attributes of the instrument 106. According to one embodiment, the instrument operating condition may include a condition indicative of a condition-dependent status of the instrument 106. For example, the condition-dependent status may be indicative of a physical condition of the instrument 106. In this regard, for the sake of non-limiting example, the condition-dependent status may correspond to the physical condition of a drive system of the instrument 106. The data collection module may therefore be configured to identify such instrument operating condition, for example, by comparing a data value measured at first sensor 122 (e.g., the operating temperature of the drive system) with an accessed data value of the thresholds/conditions database 150 (e.g., corresponding to a normal operating temperature range for the drive system). Accordingly, the condition-dependent status may be at least partially based on this comparison of values (e.g., the condition-dependent status may indicate that the noted drive system "Needs Servicing" or any other appropriate indicators in relation to the foregoing comparison).

In yet another embodiment, the instrument operating condition may be indicative of an inventory-dependent status. As noted, in some instances, the working tool 102 may be one of a plurality of working tools associated with the system 100, each receivable by the instrument 106. In this regard, it may be desirable for a user of the system 100 to receive an indication in relation to the quantities of working tools 102 of the plurality of working tools remaining within the system 100 for associable use with the instrument 106. To facilitate the foregoing, the data collection module 148 may receive data over the one or more data networks 116 corresponding to identifiers received at the instrument 106. For example, the identifier may be a working tool serial number that uniquely identifies the respective working tool 102 received by the instrument 106. The unique identification of the working tool may, in turn, be compared against a predetermined inventory level of working tools in order to account for the use of the instant received working tool 102.

In some embodiments, a machine readable indicium on a working tool may be read by a machine readable indicia reader 108 of an instrument 106 which generates or transmits an indication of an identifier associated with the working tool and more specifically, with the machine readable indicium. In this regard, the identifier may be a serial number or any other unique identification mechanism associated with the working tool to distinguish the particular working tool from other, perhaps similar, working tools. In this sense, the word "unique" is intended to indicate only that the identifier is unique within a given set of working tools and need not be entirely unique in a global sense.

Upon engagement of a working tool with an instrument 106, the identifier (e.g., serial number) of the working tool may be read and stored in a database. Such a database may be locally disposed in the instrument 106 or in a controller 112 associated with the instrument 106, remotely disposed in a database in operative communication with a plurality of instruments, or in a global database in communication with all instruments capable of engaging the working tools described herein, for example. The identifier of a given engaged working tool may be referenced against such a database prior to operation of the instrument 106. In this regard, if the identifier is found in a database which contains identifiers of previously used working tools, certain conditions may be placed upon operation of the instrument 106. For example, if a working tool is considered to be a one-time use or disposable device, then the instrument 106 may be prevented from operation based upon a determination that an engaged working tool has been previously used, locally or remotely (such as with another instrument at another facility). In the case that a working tool is designated or approved for only a single use, such as in a thresholds/conditions database, any subsequent attempts to utilize the working tool after an initial registration with an instrument may be denied by a controller. As another example, certain working tools may be restricted to a single patient or may be associated with a maximum operational life. In the former regard, each time a working tool is engaged with an instrument 106 (or more or less frequently), a database may be referenced to determine if the given working tool has been used on another patient. If so, the instrument 106 may be prevented from engaging the drive motor based on a control signal, or lack thereof, received from the controller 112. In the latter regard, each time an instrument is operated, the time elapsed during use may be recorded in a database which maintains total use times of each working tool. A rule (stored for example, in thresholds/conditions database 150) may be used to establish a maximum operational life such that at any time the total use time of a particular working tool reaches or exceeds the maximum operational life, all instruments associated with that working tool may be prevented from further operation if the working tool is engaged therewith.

A controller 112 may be operable to send a request to a remote server including a working tool identifier. The remote server may utilize the identifier to process rules, lookup data associated with the identifier, and/or transmit an output back to the controller 112. In response to receipt of the output, the controller 112 may be operable to restrict or permit operation of the instrument 106. Alternatively, a remote server may not be utilized. Rather, the controller 112 may itself be operational to lookup data associated with a working tool identifier, to process rules which determine operation limitations, and implement policies in accordance with the rules to permit or restrict operation of the instrument 106. For example, the controller 112 may be in operative communication with a drive motor of the instrument 106. In the absence of the receipt of a working tool identifier at the controller 112 (which may indicate a counterfeit, unapproved, improperly refurbished, or otherwise incompatible working tool), or in the event that an identifier is associated with an unacceptable condition (e.g., the working tool has been previously used and is therefore incompliant with standards of care), the controller 112 may prevent engagement of the drive motor. Similarly, a rule may indicate that the identifier is associated with a limited operating speed. In response, the controller 112 may limit the speed of the drive motor of the instrument 106.

In still other embodiments, a database of standard operations, such as surgical procedures or medical operations may be maintained locally or remotely. A user may select a standard operation at an access terminal 118 in communication with a given instrument 106 or set of instruments. The standard operation may be associated with a set of rules or other specifications regarding working tools that may be used in accordance with standard operating procedures. For example, a particular type of operation (e.g., ACL reconstruction) may require or otherwise be associated with working tools having a particular material composition, a particular manufacturer, a given range of diameters and/or lengths, etc. for compliance with regulations or standards of care. In this regard, an instrument may be associated with an operation, for example, by manual data entry into the access terminal. Upon engagement of a working tool with the instrument, the database may be referenced to determine if the attributes of the working tool engaged with the instrument are compatible with the instrument and/or meet the specifications of the operation. If the attributes comply with the requirements of the operation, a drive motor of the instrument may be allowed to operate. If one or more attributes of the working tool, as determined based upon the identifier, do not comply with the requirements of the operation, the drive motor may be prevented from engaging and/or an alert to the user may be triggered.

In some instances, working tools or other medical devices used during surgery may become misplaced and in a few cases, may be unintentionally deposited within a surgical site of a patient. In order to ensure all working tools are accounted for upon completion of a procedure, inventory may be taken. To facilitate such inventory accounting, a list of working tools used during a procedure may be maintained in a local or remote database. Upon completion of the procedure, the list may be used to manually or automatically take inventory of used working tools. For example, each working tool engaged with an instrument used during the procedure may have a unique identifier which is maintained in a list of used working tools. The list may be presented to a user on a display of an access terminal for manual verification that all used working tools are accounted for. Additionally or alternatively, a machine readable indicia reader (either disposed in an instrument or independently) may be utilized to scan or otherwise read the machine readable indicium of each working tool collected upon completion of the procedure. If an identifier is present on the list of used working tools (thereby indicating the associated working tool was used during the procedure) but the working tool associated with the identifier is not scanned upon completion of the procedure, an alert may be triggered to the user via an instrument, a controllers, access terminal, etc. In certain other embodiments, the instrument operating condition may be indicative of an environment through which the working tool 102 is advanced during use, including one or more characteristics of the environment such as environment density. In this regard, the data collection module 148 may process one or more data attributes measured by, for example, the first or second sensors 122, 124 in order to obtain information in relation to the environment through which the working tool 102 is advanced. For example, according to one embodiment, the first sensor 122 may be configured to measure the displacement of the working tool 102 relative to an axis along which the working tool 102 is advanced during use. Additionally, the second sensor 124 may be configured to measure the force presently applied at the working tool 102. In this regard, the instrument operating condition, as identified by the data collection module 148, may be at least partially based on the measured displacement of the working tool 102 and the measured forced applied at the working tool 102.

As such, the instrument operating condition may be indicative of a density of the environment through which a working tool of the instrument is advanced during use. In this regard, the instrument operating condition may dynamically change with the operation of the instrument 106. For example, the working tool 102 may be advanced through an environment with a variable density or through an environment with several discrete changes in density. As such, the instrument operating condition may be compared in real time to one or more data values which may be stored, for example, in thresholds/conditions database 150 in order to facilitate the provision of an alarm output in relation to the identified instrument operating condition. For example, as described above in relation to alarm 130, an alarm output responsive to the comparison of the identified instrument operating condition with the one or more parameter values may alert a user to a condition of interest and/or prompt a user to take various corrective actions.

Figure 13:
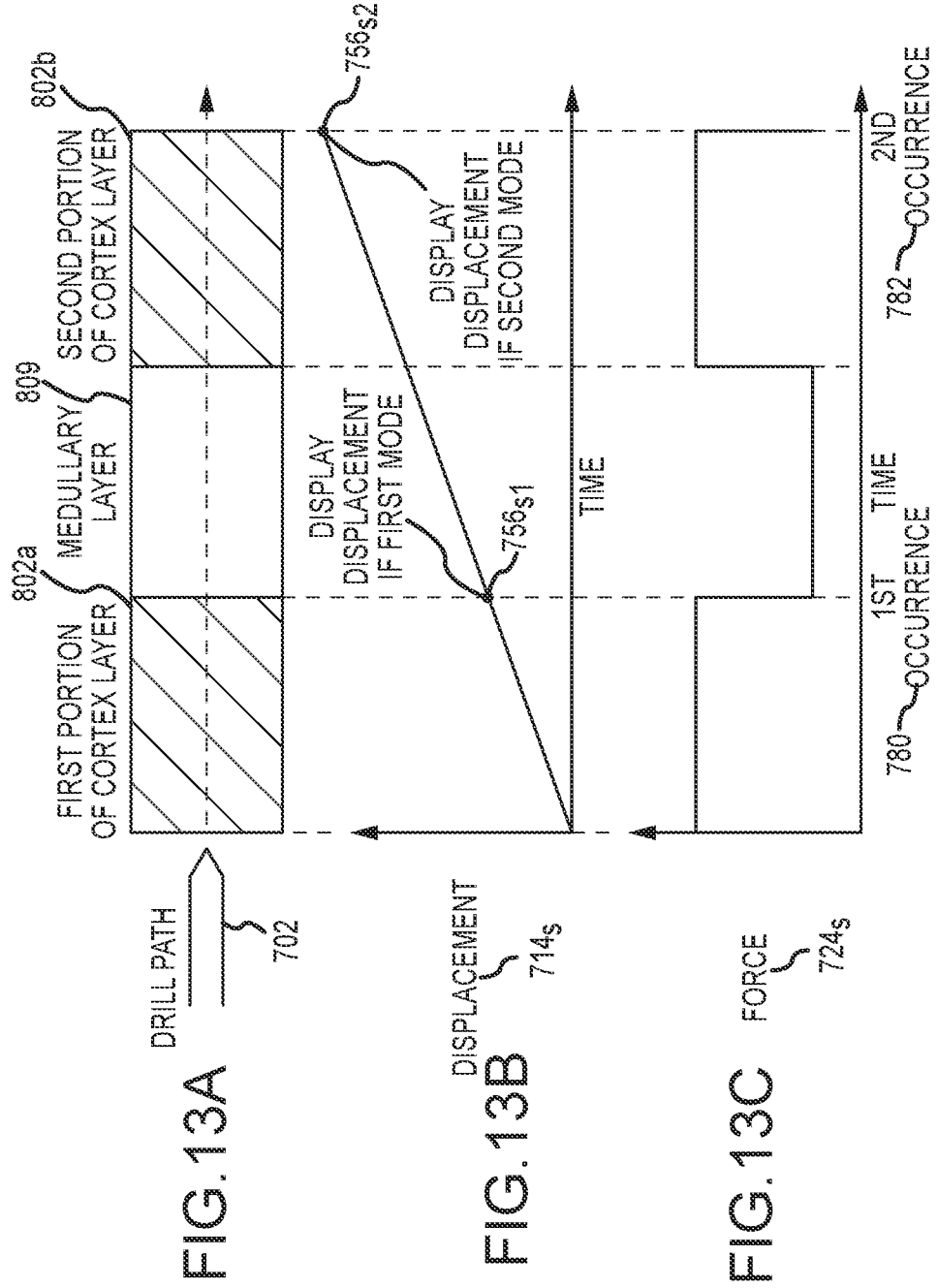
FIGS. 13A, 13B, and 13C are diagrams illustrating the position of the drill bit of FIG. 7 in bicortical bore of FIG. 8B and the corresponding output of the first and second sensors of the displacement and load measurement assemblies of FIG. 2.

To illustrate the foregoing, consider that the instrument 106 may be embodied as a surgical instrument disposed for measuring the displacement of a received working tool 102 relative to an exterior surface of a surgical site during a surgical operation. In this regard, the working tool 102 may be embodied as a surgical drill bit. Accordingly, the instrument operating condition may be configured to be indicative of a bone density. As will be described in greater detail below, the particular value of the bone density through which the working tool 102 is advanced may be indicative of various stages of a surgical procedure involving various stratums of tissue, as depicted in greater detail in FIGS. 13A-13C). In this regard, the instrument operating condition may support aspects of the surgical operation by alerting the user to particular changes in bone density that may prompt various corrective actions.

In some instances, the particular value of the instrument operating condition may be compared for analysis with one or more threshold values in order to provide an alarm output corresponding to a condition of interest. That is, one or more threshold values or conditions may be associated with a change in bone density that prompts the corrective action by the user. Notably, however, the particular threshold value of bone density may be different for each subject of a medical operation based on demographics, medical conditions and history, or other individualized characteristics. Accordingly, the data collection module 148 may be operable to associate the instrument operating condition with one or more health history characteristics of the subject. That is, the data collection module 148 may access one or more particular health history characteristics of the particular subject undergoing the surgical operation to determine a threshold value for the instrument operating condition in order to facilitate the provision of an alarm or other appropriate output. In this regard, the data collection module 148 may compare the instrument operating condition to a particular subject's health history characteristic, which may include a subject's age, weight, sex, nationality, geographic location, medication history, disease history, and/or any other appropriate characteristic that may facilitate the identification of an appropriate threshold value for comparison with the instrument operating condition indicative of bone density. In some instances, this may include execution of one or more algorithms as described above in relation to alarm module 130 of instrument 106.

In certain other embodiments, the controller 112 may also include analytics engine 158 in operative communication with the data collection module 148 and configured to analyze the identified instrument operating condition and/or the received identifier as identified or received at either the controller 112 or the instrument 106. For example, the analytics engine 158 may generate one or more metrics displayable at a user portal, in order to facilitate the disclosed monitoring of instrument 106. In this regard, the analytics engine 158 may provide information for use in taking corrective actions in response to the identified instrument operating condition and/or received identifier. Furthermore, the controller 112 may also include a portal 160 such as an Internet or web-based platform to facilitate transmitting information associated with identifying the instrument operating condition and/or the working tool attribute to access terminal 118. In some embodiments, the controller 112 may receive data from the access terminal 118 via the one or more data networks 116.

In another embodiment, the controller 112 is one of a plurality of controllers 112 that collectively communicate to form a distributed network. In this regard, each of the plurality of controllers 112 may be in operative communication with a central processing server (not pictured) remote from the plurality of controllers 112. Each of the plurality of controllers 112 may also be in operative communication with a respective instrument 106 or a plurality of instruments and able to identify an instrument operating condition and/or received identifier associated with the respective instrument. As such, information from each of the controllers 112 may be sent to the central processor to analyze one or more parameters. For example, each of the controllers 112 may transmit information to the central processor in relation to a particular identified instrument operating condition of interest, such as bone density for a respective subject undergoing a surgical operation with the respective instrument, etc.

By way of continued example, the controller 112 may transmit the measured bone density with regards to identified subjects that correspond to the specified medical history of the patient. In this regard, the central processor may aggregate such information in order to determine an aggregate threshold value for identifying an instrument operating condition value that will facilitate the provision of an alarm output for a subject with similar medical history characteristics. For example, this aggregated value may result in the determination of one or more correlation factors that may be transmitted to one or more controllers. In this regard, upon the subsequent operation of the instrument 106, the controller 112 may be configured to generate a response based on an identified instrument operating condition as analyzed with respect to the received correlation factor. As such, the controller 112 may leverage the information received at the central processor in order to more accurately identify the instant instrument operating condition. This may be accomplished by executing a predictive algorithm based on the correlation factor to predict an instrument operating condition in a particular use case of the instrument 106, for example.

The embodiments of a controller 112 and instrument 106 are provided for exemplary illustration only. Certain components illustrated in FIG. 2 as being part of instrument 106 may optionally be disposed in controller 112. For example, processing engine 120 may be the same as processing engine 140. In this regard, all operation of the instrument may be processed by processing engine 140 of the controller 112 which may or may not be disposed within instrument 106. Furthermore, data collection module 126 may be data collection module 148, communications module 132 may be communications module 143, and storage 128 may be storage 142. Furthermore, alarm 130 may be disposed within controller 112.

Figure 3:
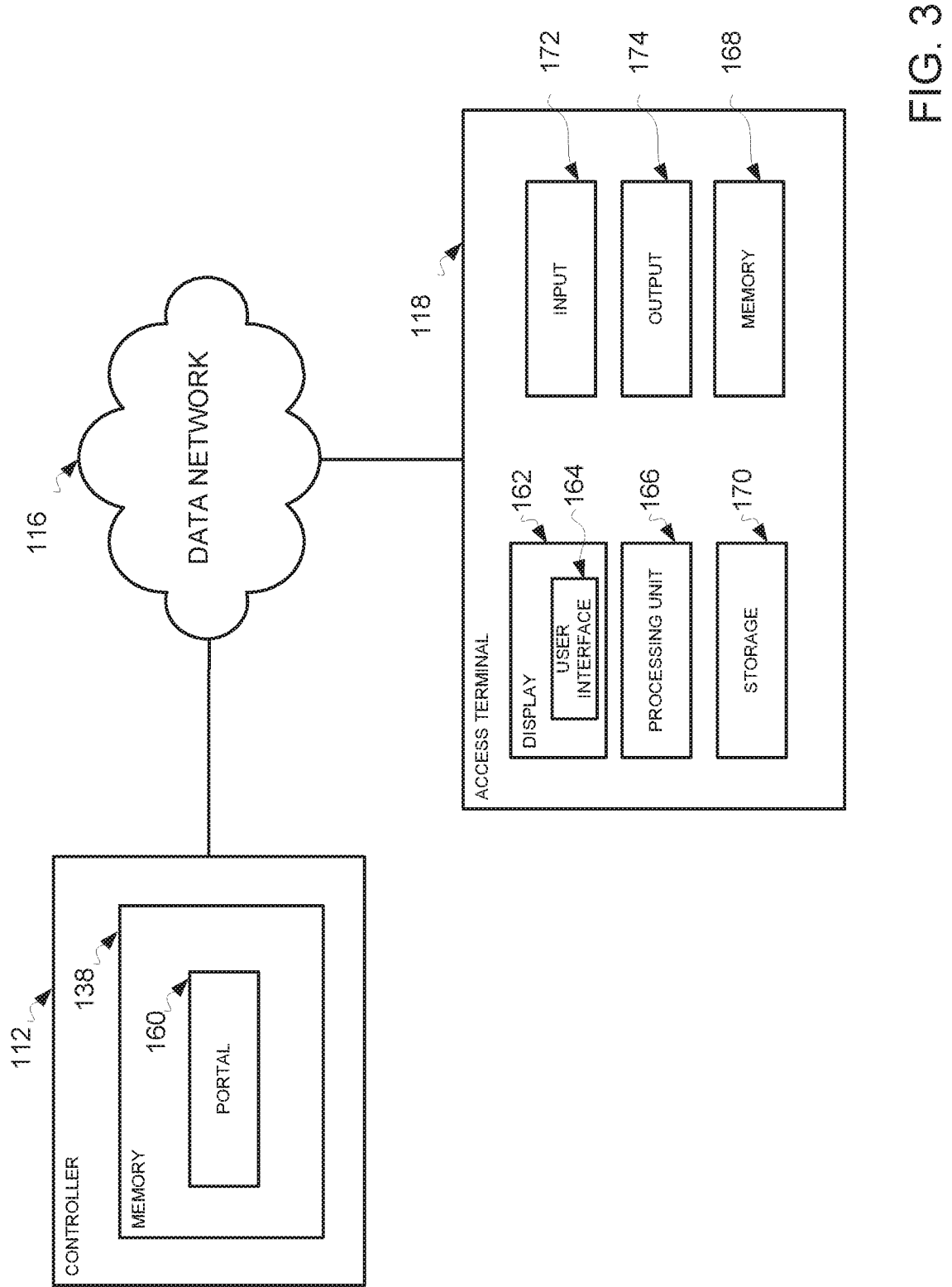
FIG. 3 is a functional block diagram of an access terminal for use in a system for monitoring an instrument, according to one embodiment.

Turning next to FIG. 3, a more detailed functional block diagram of the access terminal 118 for use in receiving and transmitting information with the controller 112 is depicted. The access terminal 118 may generally employ various components to receive and transmit information. In this regard, as shown, the access terminal 118 may include a display 162 that presents information associated with the controller 112 to a user via a user interface 164; processing unit 166 configured to process received information; memory 168; and storage 170 for storing received and/or processed information. Additionally, the access terminal 118 may be configured to receive input 172 in response to information presented on display 162 and transmit output 174 which may be indicative of a request for information from the controller 112, etc. . . . . In this regard, the controller 112 may transmit information between the portal 160 and the access terminal 118 via the one or more data networks 116. For example, this may occur by any appropriate browser (not shown) running on the memory 168 of the access terminal 118 that may appropriately access the portal 160 via the one or more data networks 116.

Reference will now be made to a number of representative screen shots of the portal 160 that may be presented on, for example, display 162 of the access terminal 118 and that may be manipulated by a user to configure the monitoring of the instrument 106 as described in detail below. It should be understood that the various functionalities disclosed herein are not limited to use with such specific screenshots as presented. Rather, the screen shots are merely provided to facilitate the reader's understanding of the various programs, modules, and other functionalities disclose herein.

Figure 4:
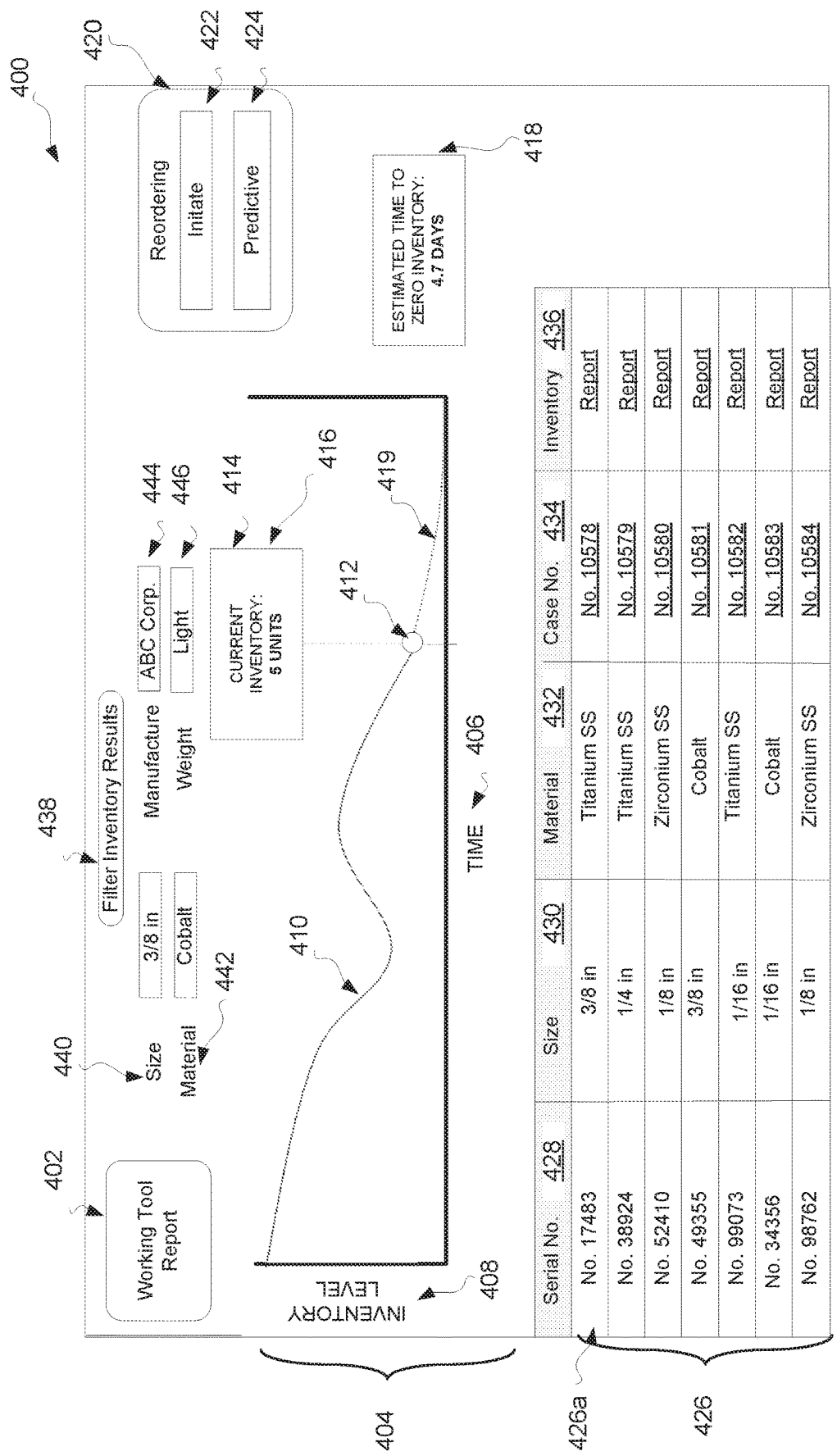
FIGS. 4 and 5 illustrate various screenshots of embodiments of a user interface displayable via a portal of a system for monitoring an instrument.

Starting now with FIG. 4, a screenshot 400 is depicted in which a working tool report 402 is displayed. Broadly, the working tool report 402 may include various configurations of information for use in identifying an instrument operating condition, such as an inventory-dependent status. As noted, the respective working tool may be one of a plurality of working tools receivable by the instrument 106. In this regard, it may be desirable to present information in relation to the usage of the plurality of working tools.

According to one embodiment, the working tool report 402 may include inventory level monitoring graph 404 for use in displaying the foregoing information in a graphical format. In this regard, the inventory level monitoring graph 404 may include a time axis 406 (shown extending generally along an x-axis in the illustrative example) and an inventory level axis 408 (shown extending generally along a y-axis in the illustrative example).

To illustrate the foregoing, the inventory level monitoring graph 404 may include one or more graphical lines. For example, the inventory level monitoring graph 404 may include aggregate working tool inventory line 410 indicative of an aggregate inventory level of the plurality of working tools which may indicate a total count of the plurality of working tools available for association with the instrument, as filtered by various user criteria as a function of time. According to one embodiment, each received identifier of a respective working tool at the instrument may facilitate the identification of the inventory-dependent status of the instrument operating condition. For example, the data collection module may decrease the inventory-dependent status for each received identifier which is indicative of the working tool being utilized such that it cannot subsequently be associated with the instrument 106 after the instant use. In this regard, the aggregate working tool inventory line 410 may generally decrease over a period of time with each subsequent use of a respective received working tool, as represented with respect to the time axis 406. Alternatively, the aggregate working tool inventory line 410 may periodically increase. For example, the identified inventory-dependent status may be updated based on a restocking or resupply of the plurality of working tools.

The inventory level monitoring graph 404 may facilitate the dynamic or substantially real-time monitoring of the inventory-dependent status via the aggregate working tool inventory line 410. For example, the aggregate working tool inventory line 410 may include current inventory level 412. In this regard, the inventory level monitoring graph 404 may provide an indication to a user of the system indicative of the inventory level of working tools associable with the instrument 106. In some instances, the current inventory level 412 may be accompanied by a floating box 414 operable to provide additional information in relation to the current inventory level 412. In this regard, according to one embodiment, the floating box 414 may include current inventory status indicator 416.

More generally, working tool report 402 may include other indicators or visual modules to facilitate the dynamic or substantially real-time monitoring of the inventory-dependent status. For example, the working tool report 402 may include "zero" inventory indicator 418 configured to provide an indication in relation to the estimated time until the current inventory level 412 will be equal to zero units (assuming that additional working tools 102 are not subsequently added to the plurality of working tools 102). In this regard, the zero inventory indicator 418 may be based on a variety of measured and determined factors including the rate at which the inventory of the plurality of working tools 102 is depleted. In some instances, the rate at which the plurality of working tools 102 is depleted may be represented at inventory level monitoring graph 404 by anticipated inventory level line 419. In this regard, the anticipated inventory level line 419 may be configured to project the aggregate inventory level based on an analysis of historical inventory levels which may include reference to data stored at past performance database 152, etc. Accordingly, the foregoing functionalities may prompt a user to take corrective actions to facilitate maintenance of an appropriate inventory level of the plurality of working tools 102 associable with the instrument 106.

Such corrective actions may be facilitated by the functionality of the working tool report 402. For example, the working tool report 402 may include reordering button 420 to facilitate the replenishment of the inventory level of the plurality of working tools 102. In this regard, the reordering button may be manipulated by a user to increase the inventory level. In this regard, reordering button 420 may include initiate bar 422 configured to accept a response from a user that causes initiation of a preprogrammed ordering protocol. As such, the inventory level may be manually increased by the manipulation of the initiate bar 422. In this regard, in some instances, manipulation of the initiate bar 422 may trigger a variety of events, such as, placing an order for the additional inventory, assigning the inventory to a physical location, and/or other appropriate logistical functions.

Furthermore, the reordering button 420 may also include predictive bar 424 configured to accept a response from a user that causes initiation of a preprogrammed ordering protocol to automatically increase the inventory level of the working tools 102. For example, the data collection module 148 may monitor one or more parameters displayable at the working tool report 402 in order to determine an appropriate time at which to initiate a preprogrammed ordering protocol to increase the inventory level of the plurality of working tools 102.

Working tool report 402 may also facilitate displaying information in relation to various working tools 102 of interest. In this regard, the working tool report 402 may include detail inventory display 426 configured to display various details associated with a particular, or subset of, working tools 102 of the plurality of working tools 102. In the illustrated embodiment, the detail inventory display 426 may include a serial no. column 428, a size column 430, a material column 432, a case no. column 434, and an inventory column 436. It will be appreciated, however, that in other embodiments, more or less columns may be included at the detail inventory display 426 as may be appropriate and/or of interest to a user in relation to the characteristics of a particular working tool 102.

Consider, for the sake of illustration, row 426a of detail inventory display 426, which displays various information attributes associated with a working tool 102 uniquely identified by serial number 17483, according to serial number column 428. In particular, row 426a includes information pertaining to various characteristics of the working tool 102 identified by serial number 17483. For example, the working tool identified by serial number "17483" may be associated with a size of "⅜ inch" and be associated with a material of "Titanium SS". In some cases, the working tool 102 may be prospectively assigned to a use case (e.g., a planned use of the working tool 102 for a particular case or scenario, such as a particular planned surgery, etc.). In this regard, the working tool 102 identified by serial number 17483 may be associated with prospective use case number "10578". In some instances, the data value depicted at the case no. column 434 may be manipulable by a user such that additional information may be presented in relation to the respective use case number. In other words, manipulation of the value of the case number value No. 10578 may present information to a user in relation to an upcoming surgery during which the working tool 102 identified by serial number 17483 may be scheduled for use, etc.

In some instances, the user may desire to obtain information pertaining to the inventory level of a particular subset of working tools 102. In this regard, the user may manipulate a "Report" link in row 426a in order to display information in relation to an inventory-dependent status corresponding to the plurality of working tools that share one or more particular characteristics of the working tool 102 identified by serial number 17483. In this regard, the detail inventory display 426, may facilitate the provision of additional information in relation to the inventory level of working tools with characteristics similar to the characteristics of the working tools 102 listed at the detail inventory display 426.

Additionally, the information displayed at the inventory level monitoring graph 404 may be manually filtered according to the preferences of a system user. In this regard, the working tool report 402 may include a filter inventory results button 438 configured to facilitate the presentation of information at inventory monitoring graph 404 in relation to the desired preferences. In this regard, the filter inventory results button 438 may include a size field 440, a material field 442, a manufacture field 444, and a weight field 446. Accordingly, each of the foregoing fields may be operable to accept a response from a user in order to facilitate the presentation of information at the inventory level monitoring graph 404 relative to the accepted responses. It will be appreciated that in some instances more or fewer fields may be configured to accept a user response according to the particular embodiment. Additionally, all fields associated with the filter inventory results button need not receive a response from a user in order to facilitate the foregoing filtering functionality.

According to the illustrated embodiment, the filter inventory results button 438 may accept a response in relation to a working tool size of "⅜ in", a working tool material of "Cobalt", a working tool manufacture of "ABC Corp.", and a working tool weight of "Light". As such, based on the foregoing received responses of the illustrated embodiment, manipulation of the filter inventory results button 438 may cause the inventory level monitoring graph 404 to display information associated with the inventory level of the subset of the plurality of working tools 102 that correspond to a size of ⅜ inch, a material of Cobalt, a manufacture of ABC Corp. and a weight of Light. In turn, each of the various metrics and other analytics devices described above may be updated to reflect the manipulation of the filter inventory results button 438.

Figure 5:
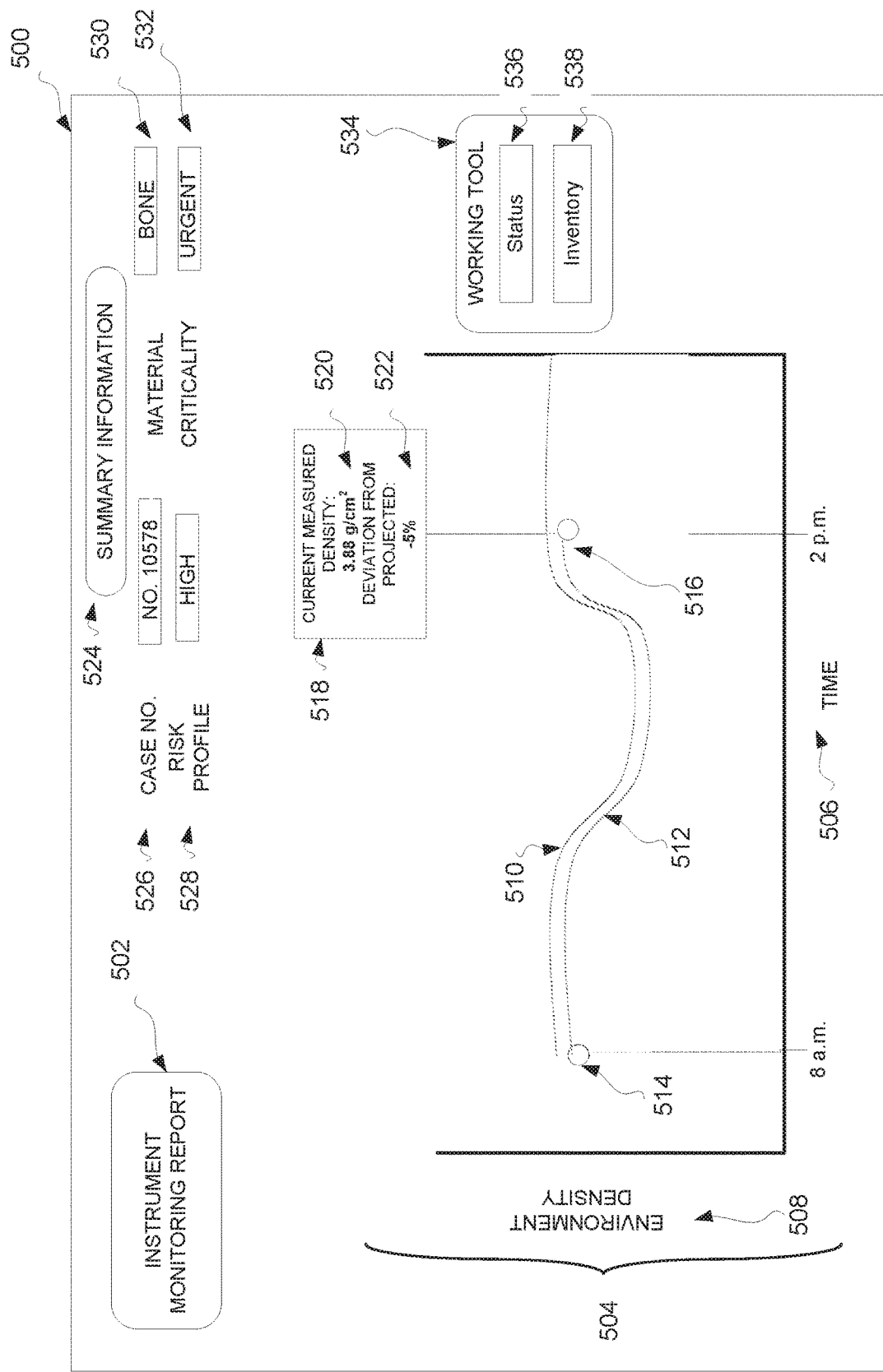

Turning next to FIG. 5, a screenshot 500 is depicted in which instrument monitoring report 502 is displayed which may facilitate the dynamic or near real-time monitoring of the instrument 106 and/or the environment through which a received working tool 102 is advanced during use, etc. Broadly, the instrument monitoring report 502 may include various configurations of information for use in displaying information in relation to an identified instrument operating condition, for example, such as the density of the material through which the working tool 102 is advanced during use. As previously described, the identified instrument operating condition may be at least partially based on data obtained from first and second sensors 122, 124 of the instrument 106 such as data indicative of a measured force applied at the working tool 102, data indicative of a measured axial displacement of the working tool 102, etc. In this regard, the instrument monitoring report 502 may be configured to present information to a user in relation to such measured data and metrics determined in relation thereto, which may prompt a user to take corrective action based on the presented information during use of the instrument 106, etc. For example, presenting information in relation to the density of the material through which the working tool 102 is advanced during use may facilitate various corrective actions in relation to the use of the instrument 106.

According to one embodiment, the instrument monitoring report 502 may include density graph 504 for use in displaying an instrument operating condition indicative of the density of the material through which the working tool 102 is advanced during use. It will be appreciated, however, the density graph 504 is only one illustrative embodiment of the contemplated functionality of the instrument monitoring report 502. In other embodiments, the instrument monitoring report 502 may include other graphs of various different identified instrument operating conditions corresponding to a condition of the instrument analogous to the functionality described herein. For example, a graph may be presented in relation to power consumption, maintenance indicator levels, and the like. In this regard the density graph 504 may include a time axis 506 and an environment density axis 508.

To illustrate the foregoing, the density graph 504 may include one or more graphical lines. For example, the density graph 504 may include anticipated density line 510 indicative of an anticipated density of the environment through which the working tool 102 is to be advanced during a particular use case. Additionally, the density graph 504 may include measured density line 512 indicative of a measured density of the environment through which the working tool 102 is advanced during use. The measured density line 512 may be based at least in part on measured values obtained at the first and second sensors 122, 124, such as forces measured at the working tool 102 and the displacement of the working tool.

The information displayed at the density graph 504 may correspond to a particular use case of the instrument 106. That is, the instrument 106 may be used for particular defined task for which the instrument operating condition is identified and analyzed. In this regard, the density graph 504 may display the anticipated density line 510 and the measured density line 512 in relation to the time or sequence of events of the particular use case. For example, at least the measured density line 512 may be displayed in relation to a start time 514 of the use case. In this regard, the start time 514 may correspond to the initiation of the particular use case of the instrument 106. As such, the measured density line 512 may increase and decrease in relation to the time axis 506 as initiated at the start time 514. The measured density line 512 may conclude at current measured density 516 indicative of the currently measured density. In this regard, as the density graph 504 may include information about the present operating condition and/or environment of the instrument 106, a user may be prompted to take corrective actions by reference to the information contained therein.

In some instances, the current measured density 516 may be accompanied by floating box 518 configured to provide additional information in relation to the currently measured density 516. In this regard, according to one embodiment, the floating box 518 may include current measured density indicator 520 to numerically indicate to a user the value of a currently measured density 516 presented at density graph 504. More generally, the density graph 504 may facilitate the comparison of a measured value with an anticipated or projected series of values. In some instances, this may be embodied as a visual comparison between various graphical lines depicted at the density graph 504. In yet other instances, the instrument monitoring report 502 may provide one or more metrics to facilitate the foregoing comparison. For example, according to the illustrated embodiment of FIG. 5, the floating box 518 may include a deviation from projected value indicator 522 to numerically indicate a percentage deviation of the measured density line 512 with the anticipated density line 510. Accordingly, the floating box 518 may prompt the user to take one or more corrective actions based on the information contained therein.

Additionally, the instrument monitoring report 502 may include summary information button 524 configured to provide one or more data parameters or characteristics in relation to the particular use case corresponding to the information depicted at the density graph 504. In this regard, the summary information button 524 may include a case no. field 526, a risk profile field 528, a material field 530, and a criticality field 532. Accordingly, each of the foregoing fields may be configured to indicate information in relation to the instrument operating condition as depicted at density graph 504. It will be appreciated that in some instances, more or fewer fields may be configured to indicate information in relation to the particular use case.

According to the illustrated embodiment, the summary information button 524 may indicate that information depicted at density graph 504 corresponds to the particular use case of "No. 10578". By way of non-limiting example, this particular use case "No. 10578" may corresponding to use of the instrument 106 in a surgical operation. In this regard, one or more parameters may be indicated in relation to the characteristics of this particular use case. For example, the use case No. 10578 may correspond to a "high" risk profile (as shown in risk profile field 528), for drilling through a "bone" material (as shown in the material field 530), during a procedure indicated as an "urgent" criticality (as shown in the criticality field 532). Notably, the information indicated at the foregoing fields may prompt the user, in conjunction with additional information displayed at instrument monitoring report 502, to take one or more corrective actions. For example, the indication at risk profile field 528 may prompt the user to operate the instrument 106 in a manner consistent with a corresponding use case.

Additionally, the instrument monitoring report 502 may be configured to provide information in relation to the working tool 102 associated with the particular use case for which the density graph 504 depicts the instrument operating condition. In this regard, the instrument monitoring report may include working tool button 534 configured for manipulation by a user to cause information to be displayed in relation to the received working tool 102. The working tool button 534 may include status tab 536 and inventory tab 538. The status tab 536 may be manipulated by a user such that the instrument monitoring repot 502 displays information in relation to the characteristics or parameter values of the working tool 102 used in the instant use case corresponding to that depicted at the density graph 504. For example, manipulation of the status tab 536 may cause information to be presented in relation to a working tool size, a working tool material, a working tool weight, a working tool manufacturer, a working tool serial number, and/or any other characteristics of interest associated with the received working tool 102. Relatedly, the inventory tab 538 may be manipulated by a user to cause information associated with an inventory-dependent status corresponding to the subset of working tools 102 that share at least some of the same attributes of the received working tool 102 of the instant use case. For example, manipulation of the inventory tab 538 may cause working tool report 402 to display information at the inventory level graph 404 that corresponds to the subset of the plurality of working tools 102 that share the same characteristics of the received working tool 102 of the instant use case. This may be desirable, for example, in order to indicate a quantity of the plurality of remaining working tools 102 that remain available for associable use for an analogous subsequent use case or may be useful in cases where multiple working tools 102 are required to complete a single use case, etc.

Figure 6:
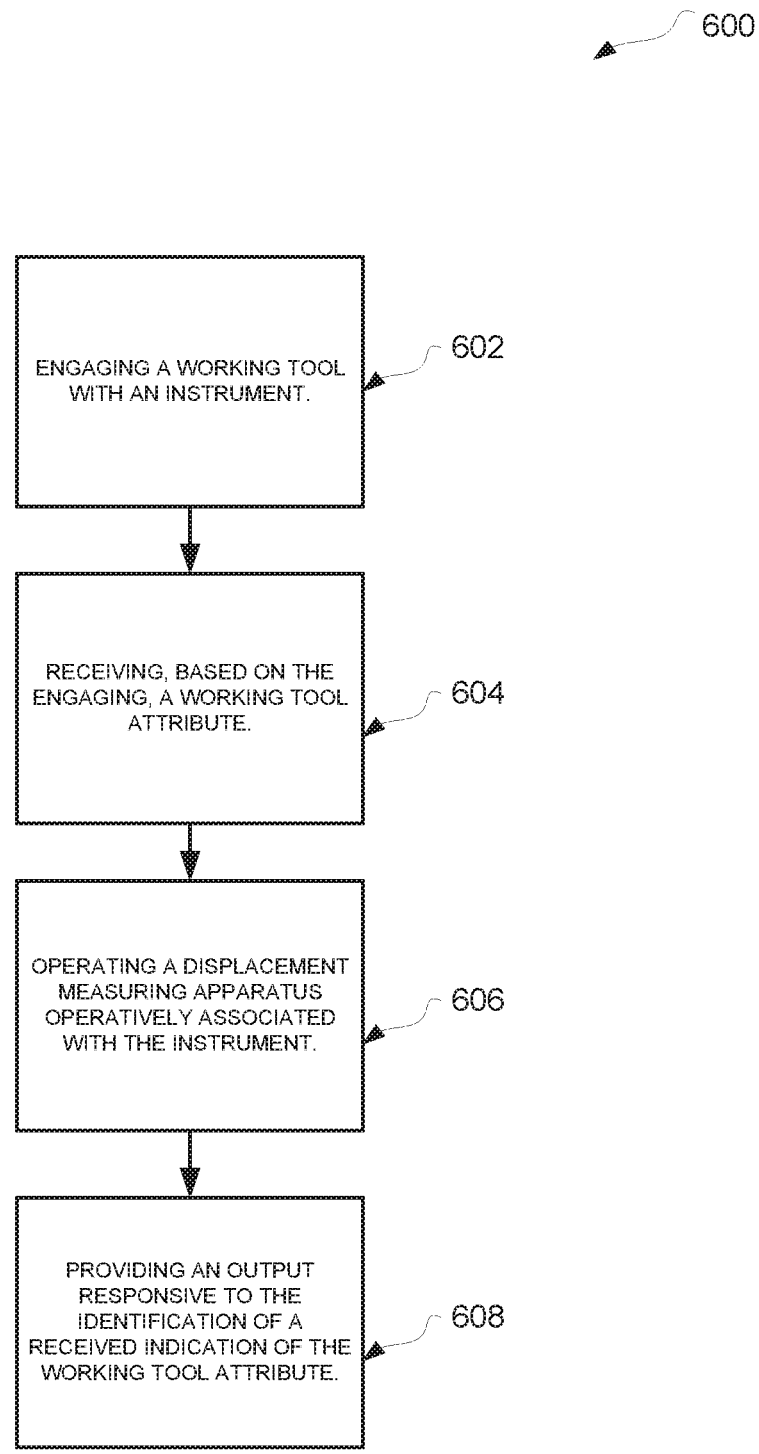
FIG. 6 illustrates with a flow diagram an embodiment of a method for monitoring an instrument.

To further facilitate the reader's understanding of the various functionalities of the utilities disclosed herein, reference is now made to flow diagram of FIG. 6, which illustrates method 600 for use in monitoring an instrument. While specific steps and orders of steps of method 600 have been illustrated and will be discussed, other methods (including more, fewer, or different steps than those illustrates) consistent with the teaching presented herein are also envisioned and encompassed with the present disclosure.

In this regard, with reference to FIG. 6, method 600 generally relates to a method for monitoring an instrument, for example, when receiving a working tool associated with one or more working tool attributes. In this regard, the method 600 may be initiated by engaging 602 a working tool with an instrument. For example, a working tool may be engaged with the instrument by advancing it into a receiving portion of the instrument. The engaged working tool may include a machine readable indicium indicative of a working tool attribute. As such, the various characteristics or parameters values that describe features associated with the particular engaged working tool may be embodied as a working tool attribute stored at the working tool itself via the attached machine readable indicium or retrievable in association therewith.

The method 600 may also include receiving 604, based on the engaging, a working tool attribute. For example, an identifier may be received at a corresponding machine readable indicia reader. In this regard, the various characteristics or parameters values that describe features associated with the particular engaged working tool may be read from or otherwise transferred from the machine readable indicium of the engaged working tool. The method 600 may further include operating 606 a displacement measuring apparatus operatively associated with the instrument. In some instances, the displacement measuring apparatus may be disposed in corresponding relation to the working tool to measure displacement of the working tool relative to an axis along which the working tool is advanced during use. In other instances, the displacement measuring apparatus may be embodied by various other sensors of the instrument that measure data for use in determining one or more operating conditions of the instrument.

The method 600 may further include providing 608 an output responsive to the received identifier. In this regard, the instrument 106 may be disposed remote from a controller or other communications and/or display device configured to indicate information in relation to the instrument.

As noted above, the foregoing functionality and system for monitoring an instrument with a working tool engaged thereby may be embodied by any number of instruments and corresponding working tools. According to one embodiment, the instrument 106 may be embodied by a drill that includes a drill bit penetration measuring system for determining, with respect to a reference point, a depth of penetration of a leading edge of a drill bit in a bore. In turn, the working tool 102 may be embodied by a drill bit that may be disposed for engagement with a chuck of the drill. In this regard, the drill bit may include a machine readable indicium indicative of a drill bit attribute such that the drill may receive an identifier of the drill bit at a corresponding machine readable indicia reader upon the receipt of the drill bit by the drill. As such, the foregoing disclosed functionalities of the system 100 may be configured for use with such drill and corresponding drill bit and accompanying measurement systems, according to embodiments described below.

As may be appreciated, certain aspects of the present disclosure may involve storage and manipulation of data in a database structure (e.g., to maintain information regarding specific working tools, operations, uses, etc.). It is presently contemplated that at least portions of such data may be advantageously provided in connection with a decentralized cryptographic distributed ledger such as blockchain. In this regard, blockchain technology may be used to capture and store data that is described herein. For instance, any data described herein may be provisioned in a blockchain such that transactions involving certain working tools may be stored and accessible for later review. Furthermore, use of blockchain technology may allow for leveraging of features facilitated by blockchain technologies such as smart contracts or the like. For instance, upon use of a working tool, the expenditure of the working tool may be noted in the blockchain, which may trigger reorder of a further working tool for a facility. Alternatively, if a supply level of working tools drops to a predetermined level, a smart contract built into the blockchain may be triggered to reorder working tools. Further still, certain information (e.g., provided via a hospital information system (HIS)) may be monitored and working tools may be automatically ordered in advance of a procedure. Such ordering may be facilitated using a blockchain. In this regard, the blockchain may be a public or private register. For instance, if information containing personally identifying information is provided, the blockchain may be private such that such information may be maintained in confidence.

In this regard, turning next to FIGS. 7-18, where like numerals indicate like elements throughout, there is shown another embodiment of the system for monitoring an instrument with a working tool engaged thereby in relation to a drill bit penetration measurement system generally designated 700, and hereinafter referred to as the "measurement system" 700, in accordance with the present invention. The measurement system 700 is for determining, with respect to a reference point (not shown), a depth of penetration of a leading edge 702a of a rotating drill bit 702 in a bore when the leading edge 702a of the drill bit 702 passes from a first medium having a first density to a second medium adjacent the first medium and having a second density. The drill bit 702 is rotatably driven by a drive 704 in a drill housing 706 of any typical well known surgical drill. In this regard and as may be appreciated below, a measurement system 700 may be provided with an existing surgical drill as a retrofit. In a further embodiment described in greater detail below, a measurement system 1000 may be provided that is at least partially integrated into a drill 1002 as shown, for example, in FIGS. 16A-16C.

Figure 8A:
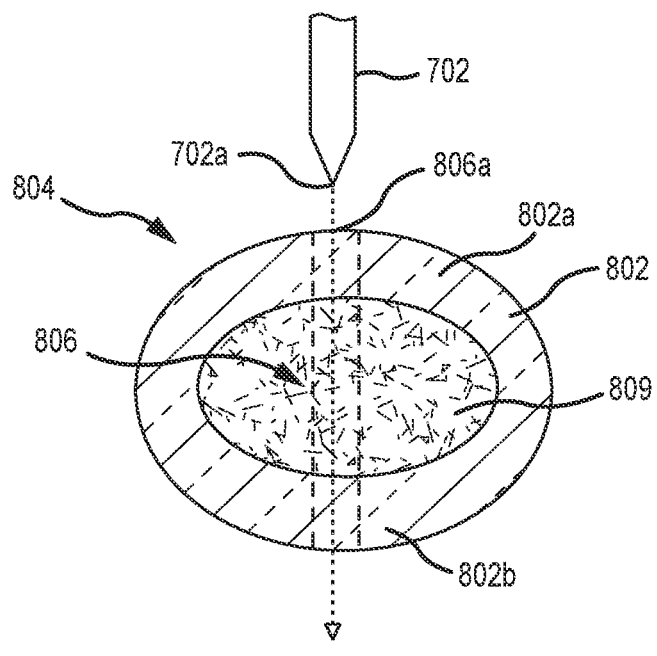
FIG. 8A is a sectional view of bone illustrating a prior art method of using a drill mechanism to create a bicortical path through a cortical bone having multiple layers.
Figure 8B:
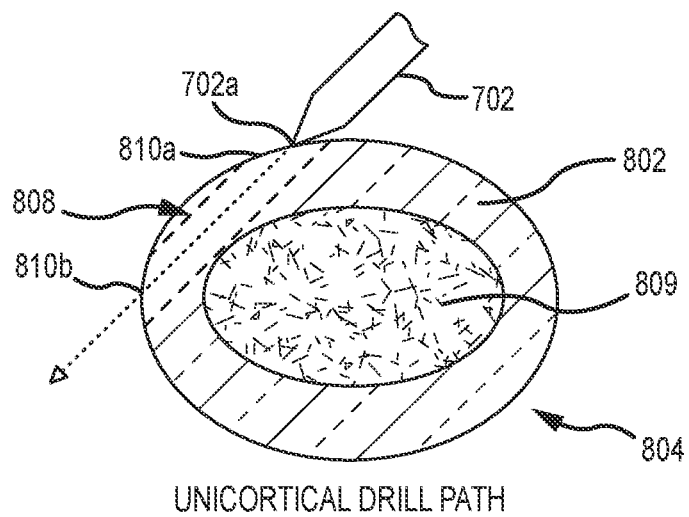
FIG. 8B is a sectional view of a bone illustrating a prior art method of using a drill mechanism to create a unicortical drill path through the outer layer of a cortical bone.

Preferably the first and second media are a hard outer cortex 802 and a medium such as air or other anatomical structure (not shown) surrounding the outer surface of the cortical bone 804 and the bore is either a bicortical bore 806 or a unicortical bore 808 being drilled in the cortical bone 804 (See FIGS. 8A-8B). However, those skilled in the art will understand from the present disclosure that the first and second media can be the hard outer cortex 802 and the soft inner medullary layer 809 of the cortical bone 804 or any adjacent media of different density without departing from the scope of the invention. The artisan will also understand that the reference point is a fixed point relative to which the displacement of the leading edge 702a of the drill bit 702 is measured and may correspond to an initial position of the measurement system 700 or portion thereof as further discussed below.

For example, as shown in FIGS. 8A and 8B, the bony structure of the human anatomy consists mainly of cortical bone 804, including hard outer cortex 802 and soft inner medullary layer 809. Following traumatic injury, plate and screw placement is critical for adequate repair of a fractured bone. Improper drilling lengths could lead to device instability, damage to anatomic structures, or device failure.

As shown in FIG. 8A, when using the rotating drill bit 702 to form a bicortical bore 806 through the cortical bone 804, the rotating drill bit 702 passes through a first portion 802a of the hard outer cortex 802, a soft non-resistant medullary layer 809, and a second portion 802b of the hard outer cortex 802.

As shown in FIG. 8B, when using the rotating drill bit 702 to form the unicortical bore 808 through the cortical bone 804, the rotating drill bit 702 passes through an entry point 810a of the hard outer cortex 802 and an exit point 810b of the hard outer cortex 802 without penetrating the soft non-resistant medullary layer 809. As such, with reference to FIG. 2, the measurement system 700 comprises a drill bit displacement measurement assembly 708, a drill bit load measurement assembly 710, and a controller assembly 712. The displacement measurement assembly 708 is connected to the drill housing 706. The connection can be made by a variety of well-known mounting methods such as a mount that clamps to the displacement measurement assembly 708 and is attached to the drill housing 706 by one or more threaded fasteners. Alternative methods such as welding or adhesive bonding could also be used. The displacement measurement assembly 708 has a first sensor 714 that outputs a first signal 714s representative of a displacement, with respect to the reference point, of the leading edge 702a of the drill bit 702 in the bore being drilled. The displacement measurement assembly 708 preferably has an extension 716 that is displaceable along a longitudinal axis. The extension 716 has a distal end 716a that can be placed in registry with the reference point when the leading edge 702a of the drill bit 702 is positioned at the entry point, such as the entry point 806a of the bicortical bore 806 or the entry point 810a of the unicortical bore 808 shown in FIGS. 80A-8B and maintained in registry with the reference point throughout the drilling process. The reference point can be any anatomical structure proximal to the desired location of the bore to be drilled. The extension 716 has a proximal end 716b that is attached to the first sensor 708. Preferably the sensor 708 is a linear variable differential displacement transducer ("LVDT").

Figure 9A:
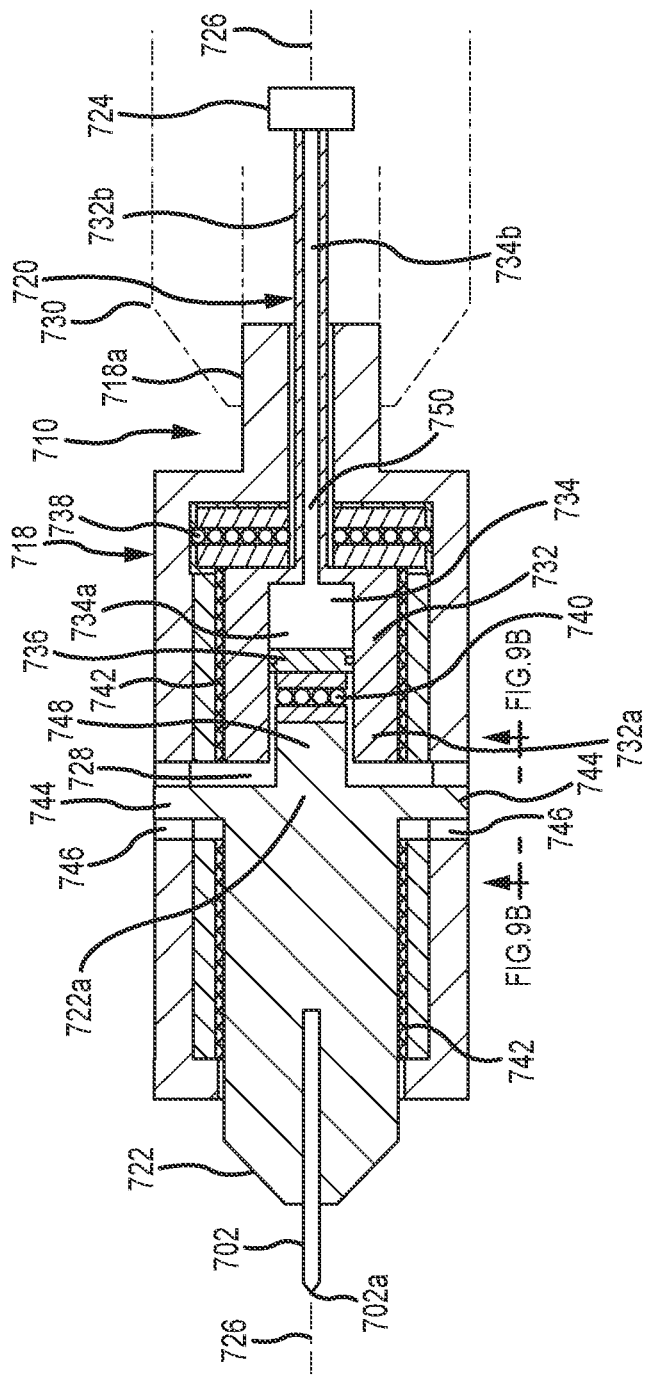
FIG. 9A is an enlarged sectional view of the embodiment of the drill bit load measurement assembly of FIG. 7.
Figure 9B:
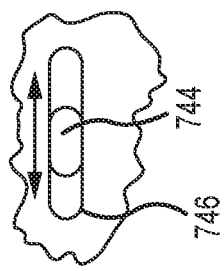
FIG. 9B is a sectional view of a portion of the drill bit load measurement assembly taken along the line 9b-9b of FIG. 9A.

Referring to FIGS. 9A and 9B, the drill bit load measurement assembly 710 comprises a housing 718, a thrust assembly 720 about which the housing 718 is rotatable, a drill chuck 722 and a second sensor 724. The housing 718 has an axis of rotation 726 and is removably connected to the drive 704 for rotation thereby. Preferably, the housing 718 has a generally cylindrical-like shape and has a chamber 728 extending the length thereof for containing a portion of the thrust assembly 720 and a portion of the drill chuck 722. Preferably, but not necessarily, the housing 718 also has a proximal end 718a with an outer diameter sized for being secured in a drive chuck 730 of the drive 704. Those skilled in the art will understand from this disclosure that the drive chuck 730 can be any well-known surgical drill chuck through which surgical instruments are insertable.

The thrust assembly 720 is preferably a tube 732 with a bore 734 therethrough. The bore 734 has a piston 736 moveable therein. The tube 732 has a first portion 732a having a first outer diameter and a second portion 132b having a second outer diameter less than the first outer diameter. Similarly, the bore 734 has a first portion 734a having a first inner diameter and a second portion 734b having a second inner diameter less than the first inner diameter. Preferably, the piston 736 is in the first portion 734a of the bore 734. The second portion 132b of the tube 720 extends beyond the proximal end 718a of the housing 718. The thrust assembly 720 is connected to the housing 718 by a first bearing 738 and to the drill chuck 722 by a second bearing 740, preferably connected to the piston 736. Preferably, the first and second bearings 738, 740 are thrust bearings suitable for use in a surgical environment. Alternatively, the first and second bearings 738, 740 could be any device that permits the housing 718 and the drill chuck 722 to rotate with respect to the thrust assembly 720 and allows a force applied to the leading edge 702a of the drill bit 702 to be transferred to the thrust assembly 720. Preferably, but not necessarily, the thrust assembly 720 also is journaled with the housing 718 by a third bearing 742.

The drill chuck 722 is connected to the housing 718 for rotation therewith and to the thrust assembly 720 for rotation with respect thereto. The drill chuck 722 is moveable in translation along the axis of rotation 726 of the housing 718. Preferably, the drill chuck 722 is a conventional surgical drill chuck having a proximal end 722a within the chamber 728 of the housing 718. The drill chuck is connected to the housing 718 by a tab 744 extending radially outwardly from the proximal end 722a of the drill chuck 722. The tab 744 extends into a corresponding slot 746 in the housing and is moveable therein in translation along the axis of rotation 726 of the housing 718. Preferably, but not necessarily, the drill chuck 722 has diametrically opposed tabs 744. Those of ordinary skill in the art will understand from the present disclosure that tabs 744 can be removably attached to the drill chuck 722 by a threaded fastener (not shown) to facilitate insertion of the proximal end 722a of the drill chuck into the housing 718. The proximal end 722a of the drill chuck 722 additionally has a projection 748 that extends into the bore 734 of the thrust assembly 720 and is connected by the second bearing 740 to the piston of the thrust assembly 720.

The second sensor 724 is connected to the thrust assembly 720 and outputs a second signal 724s representative of a force applied to the leading edge 702a of the drill bit 702. As shown in FIG. 9A, in one preferred embodiment of the present invention, the second sensor 724 is a hydraulic pressure transducer and a portion of the bore 734 forms a hydraulic chamber 750 connecting the second sensor 724 with the piston 736. As shown in FIG. 10A, in another preferred embodiment of the present invention, the second sensor 724' is a load cell, such as a piezo-electric device, adjacent the piston 736 and a portion of the bore 734 forms a conduit 750' through which passes an electrical conductor 752 connecting the piezo-electric device to the controller assembly 712.

Figure 7:
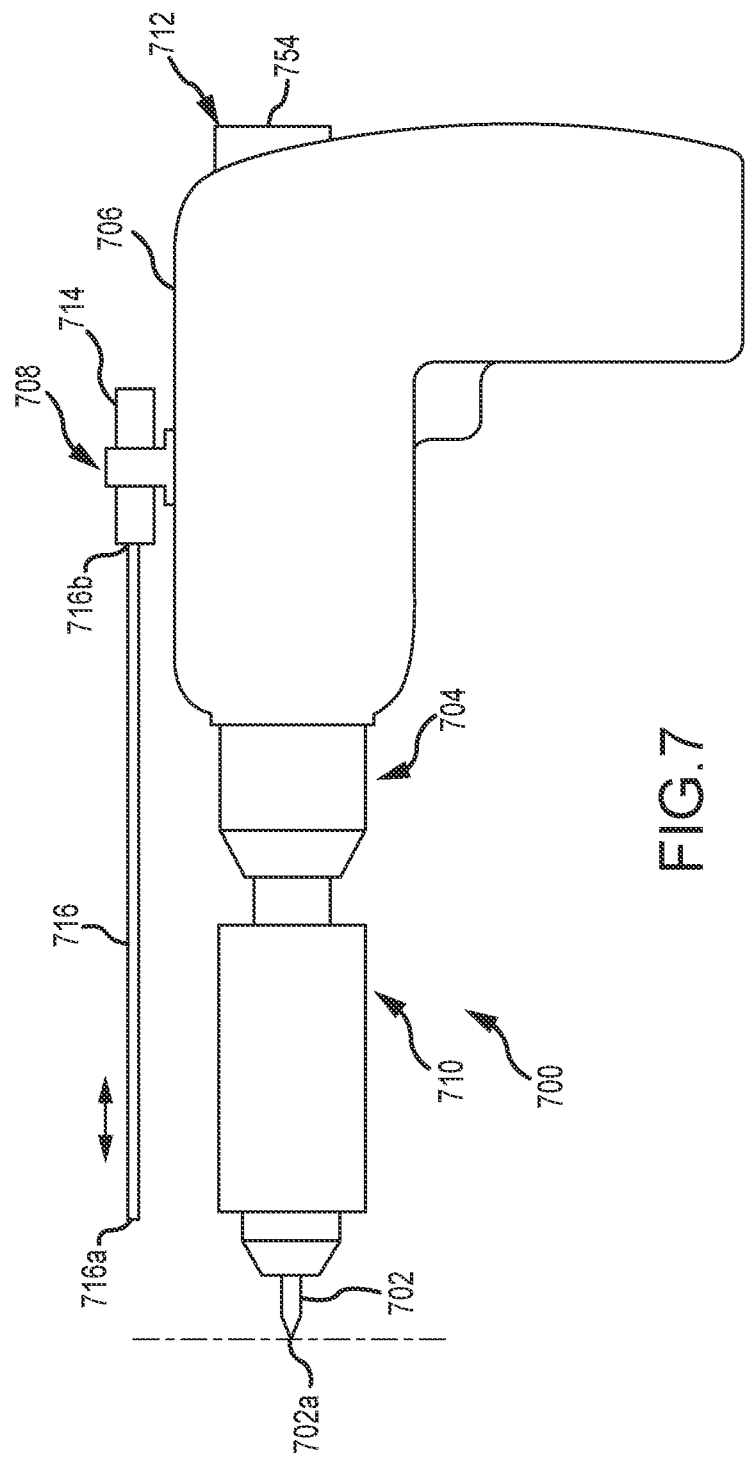
FIG. 7 is an elevation view, partially in cross section of an embodiment of a real-time, drill bit penetration measuring system.
Figure 11:
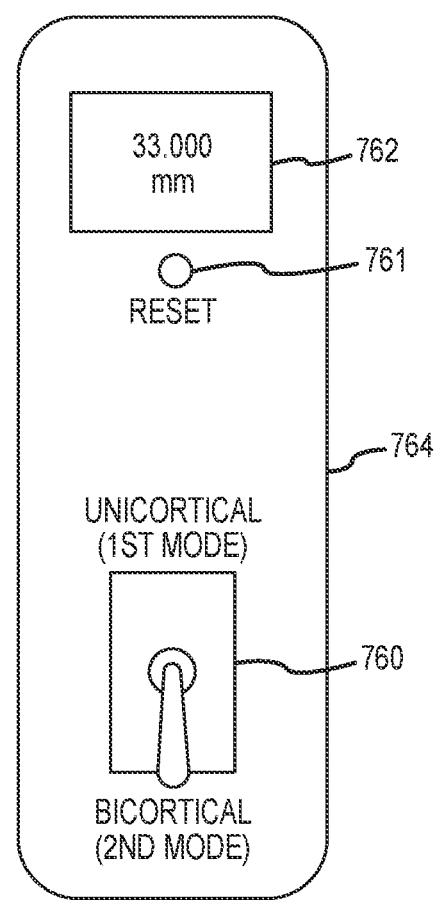
FIG. 11 is an elevation view of an embodiment of a control panel of a controller assembly of FIG. 7.
Figure 12:
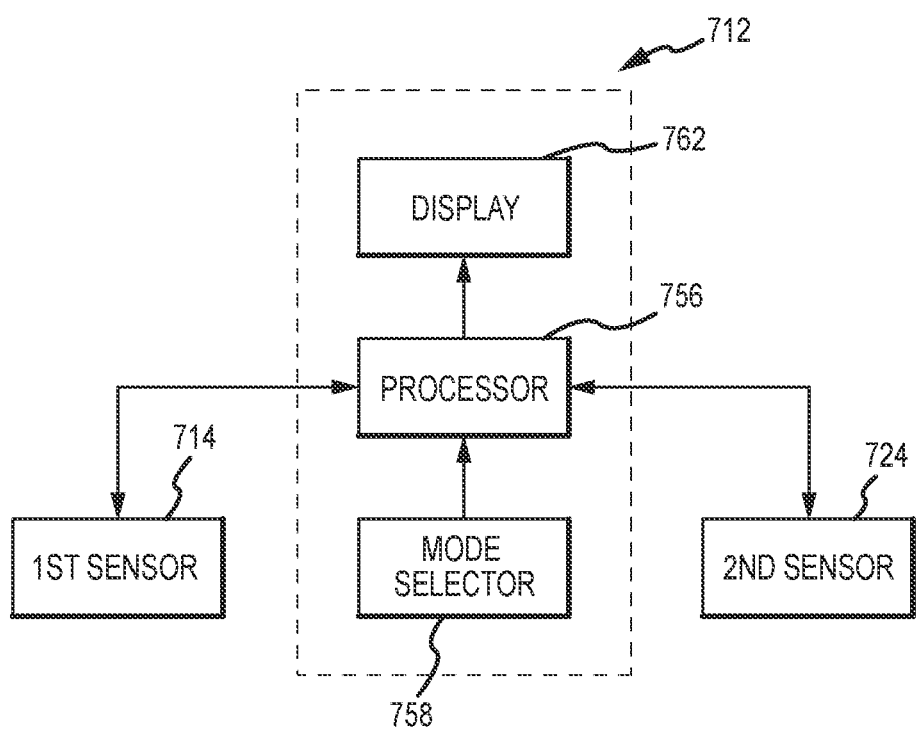
FIG. 12 is a schematic block diagram of the controller assembly of FIG. 7 and the inputs and outputs of the controller assembly.

Referring to FIGS. 7 and 11-12, the controller assembly 712 is in electrical communication with the first sensor 714 and the second sensor 724. In an embodiment, the controller assembly 712 has a controller housing 754 integral with the drill housing 706. However, with further reference to FIG. 15A, the controller housing 754 may also be provided as a remote unit. The controller assembly 712 includes a processor 756 in electrical communication with the first and second sensors 714, 724 and with a mode selector 758 having a mode selector switch 760 and a display 762 having a reset button 761. The display 762, the reset button 761 and the mode selector switch 760 may be mounted in a panel 764 of the controller housing 754. Alternatively, the display 762 or the reset button 761 or the mode selector 760 or any combination thereof could be separately housed in the remote control unit that communicates with the first and second sensors 714, 724 by a wired or wireless link. The display 762 is for indicating the measured displacement of the leading edge 702a of the drill bit 702 to the user. The display 762 is controlled by the processor 756. The display 762 may continuously indicate the changing displacement of the leading edge 702a of the drill bit 702 during the drilling of a bore and may also indicate the length of the bore at the when the drill bit 702 passes from one medium to another. In another embodiment, the remote unit may include a remote controller operable to provide an output indicative of a drill bit operating condition, as discussed in greater detail below.

For instance, with continued reference to FIGS. 15A and 15B, the display 762 may be a touch sensitive display. The display 762 may include an indication of a bore diameter 766, the drill speed 768, a drill direction 770, and a screw size indicator 772. The display 762 may also include patient information 774. The controller assembly 712 may include a port 776 for engagement of a wired plug connection 778 with the drill 1002. In other embodiments, the drill 1002 may include a wireless connection to facilitate the foregoing. In this regard, the drill 1002 may be connected to the controller assembly 712 to supply power to the drill 1002 and communicate data between the drill 1002 and the controller assembly 712.

Referring to FIGS. 7, 11-12, 13A, 13B, and 13C, the processor 756 is configured to operate in a first mode for drill bit penetration measurement in unicortical bore drilling. In the first mode the processor 756 is configured to output a third signal $756s_1$ representative of the depth of penetration of the leading edge 702a of the drill bit 702 when the leading edge 702a of the drill bit 702 passes from the first medium to the second medium. The third signal $756s_1$ is based on the first and second signals 714s, 724s. Preferably, the third signal $756s_1$ is output upon a first occurrence 780 of a second time derivative of the first signal 714s being greater than zero and a first time derivative of the second signal 724s being less than zero. In other words, a positive acceleration of the drill bit 702 and a concurrent reduction in the force applies to the leading edge 702a of the drill bit 702 trigger the first occurrence 780. At the time of the first occurrence 780, the third signal $756s_1$ corresponds to the length of the unicortical drill path.

Preferably, but not necessarily, the processor 756 is also configured to operate in a second mode for drill bit penetration measurement in bicortical bore drilling and the mode selector 758 and mode selector switch 760 are for selecting between the first and second modes. The second mode of operation is directed to the case where the first medium is the cortical bone 802 surrounded by a second medium, such as the air or tissue surrounding the outer surface of the cortical bone 802, and the first medium encloses a third medium, such as the soft medullary layer 809, having a third density. In the second mode, the processor 756 is configured to output the third signal $756s_2$ in response to a second occurrence 782 of the second time derivative of the first signal 714s being greater than zero and the first time derivative of the second signal 724s being less than zero and corresponds to the length of the bicortical drill path. Accordingly, the third signal $756s_2$ is output after the second time the drill bit 702 accelerates with a concurrent reduction in the force applied to the leading edge 702a of the drill bit 702.

Additionally or alternatively, the third signal 756s (collectively referring to 756s$_1$ and 756s$_2$ referenced above) may be at least partially based on additional parameters other than the first signal 714s and second signal 724s. For instance, in at least some embodiments, the third signal 756s may be at least partially based on a parameter associated with the rotation of the drill bit 702. For instance, the speed of the drive 704 turning the drill bit 702, the torque applied to the drill bit 702 by the drive 704, or another appropriate parameter regarding the rotation of the bit 702 may be utilized in outputting the third signal 756s. Further still, parameters such as the diameter of the drill bit 702, the bone to be drilled, or other appropriate parameters may be utilized in determining the third signal 756s.

Furthermore, the generation of the third signal 756s may at least partially be customized based on the patient. In this regard, information regarding the patient may be provided to the controller assembly 712 and utilized by the processor 756 in determining the third signal 756s. For instance, a patient's age, sex, and/or other demographic information may be provided. As may be appreciated, the demographic data of the patient may provide a correlation to expected bone density or other parameter regarding an expected property of the patient's anatomy based on the demographic data of the patient. In this regard, the demographic data may be used to correlate an expected parameter associated with the patient's anatomy (e.g., bone density) that may be used as a factor in generation of the third signal 756s. In addition, direct measurement of an anatomical parameter for a given patient may be provided directly to the controller assembly 712, thereby potentially eliminating the need to estimate the parameter based on demographic data.

Figure 14:
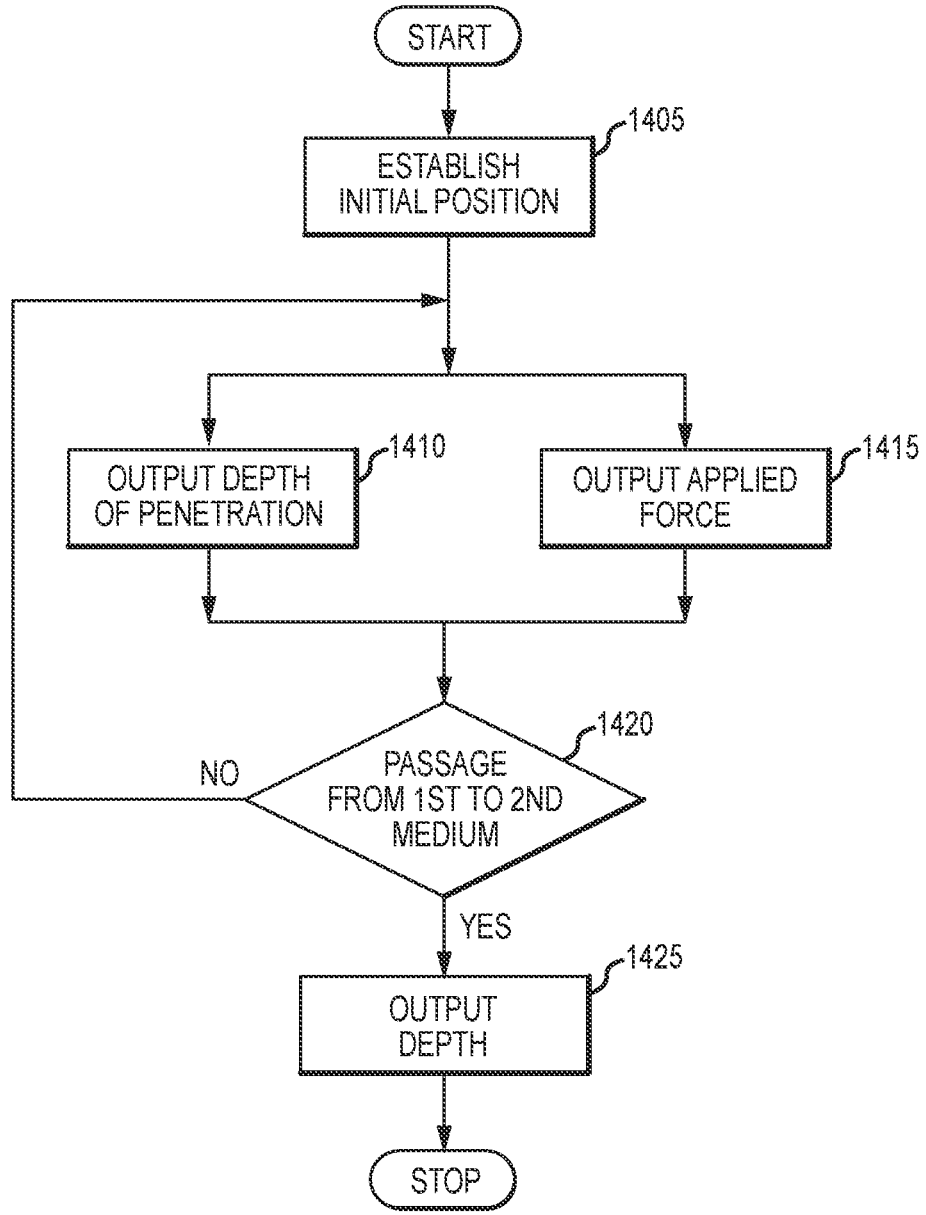
FIG. 14 is a flow diagram of an embodiment of a method for determining the depth of penetration of a drill bit.

Referring to FIG. 14, there is shown a block diagram of a first preferred method for determining, with respect to a reference point, the depth of penetration of the leading edge 702a of a rotating drill bit 702 in a bore when the leading edge 702a of the drill bit 702 transitions from a first medium having a first density, such as the hard outer cortex 802 of a cortical bone 804, to a second adjacent medium having a second density, such air or tissue surrounding the outer surface of the cortical bone 804 (FIG. 8B).

An initial position of the leading edge 702a of the drill bit 702 relative to the reference point is established (Step 1405). The initial position may be established by placing the leading edge 702a of the drill bit 702 against the outer surface of the cortical bone to be drilled and by extending the distal end 716a of the extension 716 of the displacement measurement assembly 708 to the reference point, such as an anatomical structure proximal to the desired location of the bore to be drilled. As will be appreciated in the discussion of the embodiments below, the reference point may also be established by a bushing member of a drill bit assembly that is engaged with a displacement sensing arm of a displacement sensor. With the leading edge 702a of the drill bit 702 and the measurement system reference point in the above positions (i.e., aligned at a surface of the medium to be drilled), the measured displacement of the drill bit 702 is set to zero by pressing the reset button 761. Upon commencement of drilling, a first signal representing the depth of penetration of the leading edge 702a of the rotating drill bit 702 in the bore is output (Step 1410). A second signal representing a force applied to the leading edge of the drill bit is output (Step 1415). A third signal based on the first and second signals and representative of the depth of penetration of the leading edge of the drill bit when the leading edge of the drill bit passes from the first medium to the second medium is output (Step 1420). Preferably, the third signal is output when the second time derivative of the first signal is greater than zero and a first time derivative of the second signal is less than zero.

The third signal may be accompanied by an alert that may be perceivable by a user of the drill. As such, upon determination that the drill has passed through the bone, the alert may provide feedback to the user that the bone has been drilled through. As such, the alert may be an auditory alert such as a tone or the like. In another embodiment, the alert may be a change in the speed of the motor of the drill. For instance, the drill may be slowed such that the user may be alerted to the fact that the drill has passed through the bone. Further still, the drill may be stopped at the occurrence of the third signal. It may be appreciated that any other user perceivable alert may be provided including, for example, a visual, tactic, or other type of user perceivable feedback.

Notably, the components used to construct the present invention may consist of a variety of materials that are customarily used in the manufacture of surgical drills. One having ordinary skill in the art will readily appreciate the materials that most desirably may be used to construct the present invention. In a preferred embodiment, however, the drilling mechanism, drill bit displacement measurement assembly, the drill bit load measurement assembly and the structural elements of the controller assembly may be constructed of a combination of polymeric materials, polymers, and stainless steel.

Furthermore, it may be appreciated that the spacing of the extension 716 of the displacement sensor 708 from the drill bit 702 may introduce the potential for errors or other disadvantages in determining the displacement of the drill bit 702 relative to the reference point. For instance, as the extension 716 may contact a structure that is offset from the contact point between the leading edge 702a of the drill bit 702 and the medium to be drilled. Accordingly, any movement between the structure contacted by the extension 716 and the medium to be drilled may be falsely registered as relative movement of the drill 702 with respect to the reference point. Furthermore, there may not be a rigid structure to contact adjacent to the medium to be drilled, leading to displacement of the structure contacted by the extension 716 such as in the case where the extension 716 may contact soft tissue adjacent to the medium to be drilled given the offset from the location to be drilled. Furthermore, the offset nature of the extension 110 relative to the contact between the drill bit 702 and the medium to be drilled may lead to other complications such as having to expose a greater surface of the medium to be drilled, which may adversely affect patient outcomes.

As such, an improved embodiment of a drill with an improved displacement sensor including a displacement sensing arm that extends from the drill may be provided. For example, such a displacement sensing arm may be provided that may coordinate with a bushing member of a drill bit assembly that may be used with the drill. In this regard, the bushing may move along the drill bit in a direction corresponding to the axis of rotation of the drill bit. Upon engagement of the bushing and the displacement sensing arm, the bushing and displacement sensing arm may undergo corresponding movement. As such, the bushing may be disposed in contact with the medium to be drilled when the leading edge of the drill bit is in contact with the medium. As such, a reference point may be established when the bushing and leading edge of the drill bit are both in contact with the medium to be drilled. As the bushing is located adjacent to (e.g., partially or fully surrounding) the drill bit, the bushing may facilitate contact with the medium at or very near the location to be drilled prior to creating a bore as described above. In this regard, the reference point may be more accurately maintained as the bushing may contact at least a portion of a periphery of the bore created in the medium drilled. That is, the bushing may remain in intimate contact with the medium to be drilled adjacent to the bore created. This may prevent false displacement readings attributable to the foregoing problems associated with an offset extension 110. Furthermore, the amount of contact of the drill may be localized at the location to be drilled, thus allowing for potentially less intrusion when performing drilling operations.

For example, with additional reference to FIGS. 16A-16C and 17, an embodiment of a drill 1002 comprising an embodiment of a measurement system 1000 is shown. The drill 1002 may be adapted for use with a drill bit assembly 1004 that may include a bushing 1006. The drill 1002 may integrally comprise at least some components of the measurement system 1000 to facilitate operation of the measurement system 1000 in connection with the drill 1002. For example, at least a portion of a displacement sensor 1008 may be integrated into a housing 706 of the drill 1002. In this regard, the displacement sensor 1008 may include a depth sensing arm 1010 that is specifically adapted for engagement with a bushing 1006 of a drill bit assembly 1004 that may be engaged by a chuck 1014 of the drill 1002.

In this regard, the depth sensing arm 1010 may be used to establish a reference point from which displacement of the drill bit 702 may be measured as described above. In this regard, as follows herein, a general description of the features and operation of the drill 1002 used in conjunction with the drill bit assembly 1004 is provided.

Figure 17:
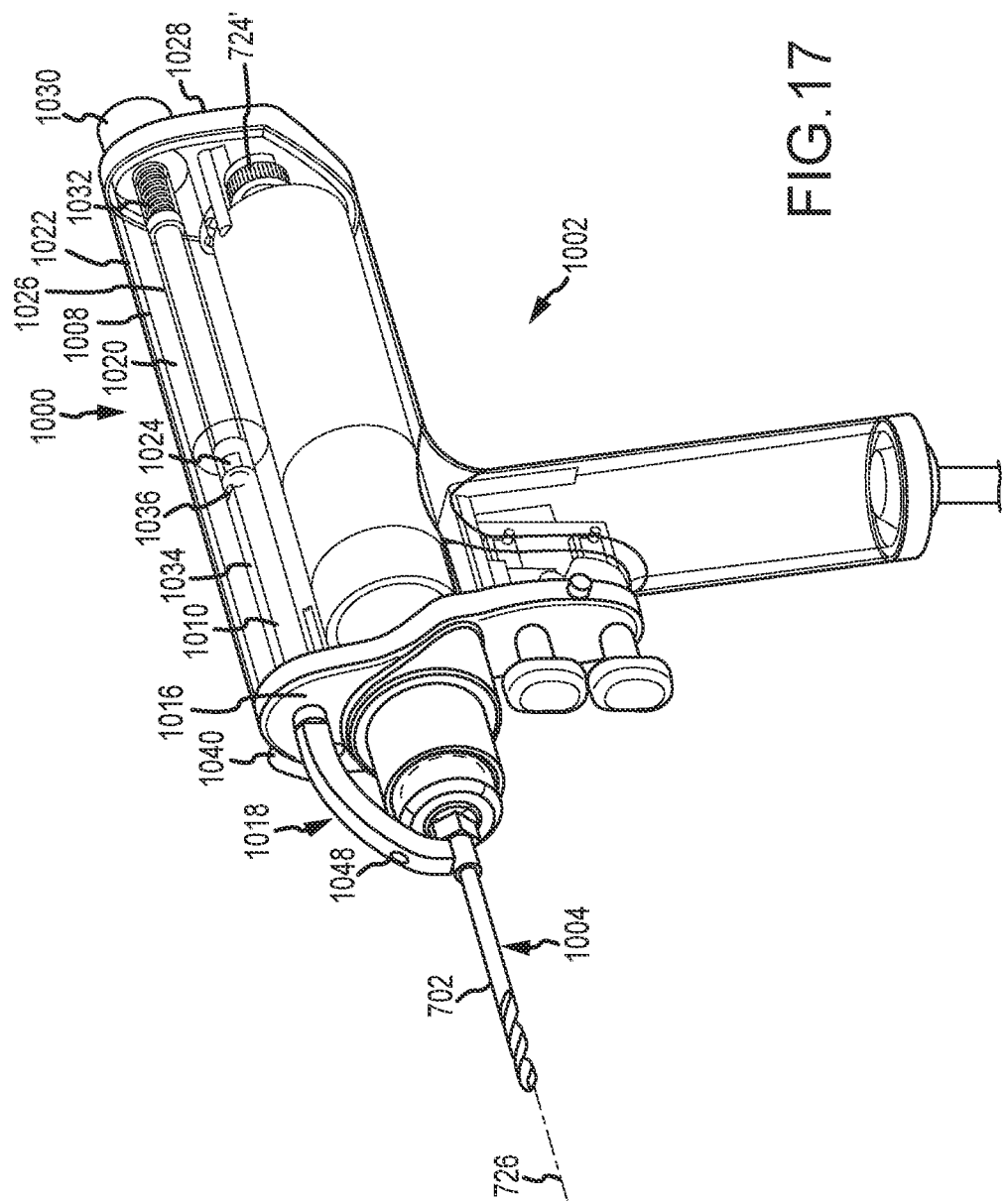
FIG. 17 is a perspective view with a partial cutaway of a drill body of an embodiment of a drill comprising a drill bit penetration measuring system.

As may be appreciated in FIGS. 16A-16C, the displacement sensor 1008 may include a depth sensing arm 1010 that may extend from the drill housing 706. For example, the depth sensing arm 1010 may extend distally (e.g., from a distal face 1016 of the drill housing 706) in a direction corresponding with the direction in which the drill bit 702 extends from a chuck 1014 of the drill 1002. At least a portion of the displacement sensing arm 1010 may extend from the drill housing 706 parallel to an axis of rotation 726 of the drill 1002. The depth sensing arm 1010 may also include a distal portion 1018 that is adapted to engage the bushing 1006 provided with the drill bit assembly 1004. As used herein, distal may correspond to a direction from the drill 1002 toward the leading edge 702a of the drill bit 702 and proximal may correspond to a direction from the leading edge 702a of the drill bit 702 toward the drill 1002. In this regard, at least a portion of the depth sensing arm 1010 (e.g., the distal portion 1018) may be adapted to engage the bushing 1006 of the drill bit assembly 1004 as will be described in more detail below. In any regard, at least a portion of the depth sensing arm 1010 may extend into the housing 706. With further reference to FIG. 17, the housing 706 may contain a coil 1020. As such, a proximal end 1022 of the displacement sensing arm 1010 may interface with the coil 1020 of the displacement sensor 1008 that may be disposed within the drill housing 706.

Specifically, in FIG. 17, the depth sensing arm 1010 is shown in a retracted position relative to the drill bit 702. As such, this retracted position shown in FIG. 17 may occur when the drill bit 702 is advanced relative to the bushing 1006 during drilling. In this regard, the proximal end 1022 of the displacement sensing arm 1010 is disposed within the coil 1020 of the displacement sensor 1008. Accordingly, the displacement sensor 1008 may comprise an LVDT sensor as described above that is adapted to sense the position of a core 1024 relative to the coil 1020. The displacement sensing arm 1010 may incorporate the core 1024 at the proximal end 1022 thereof. Accordingly, as the proximal end 1022 of the displacement sensing arm 1010 is moved relative to the coil 1020, the location of the core 1024 may be determined to provide an output corresponding to the position of the core 1024, and in turn the displacement sensing arm 1010 relative to the drill housing 706. That is, the depth sensing arm 1010 may be displaceable relative to the coil 1010 such that the displacement sensor 1008 may be operable to sense a change in position of the depth sensing arm 1010 relative to the drill housing 706 and output a measure of the displacement that may be used as described above in determining a depth of a bore. In an embodiment, the total measurable travel of the core 1024 relative to the coil 1020 may be at least about 2.5 in (6.4 cm). Furthermore, the resolution of the output of the displacement sensor 1008 may be about 0.1% (e.g., about 0.002 inches (0.06 mm) for a sensor having a total measurable travel of 2.5 inches).

While a LVDT displacement sensor is shown and described in relation to the drill 1002 shown in the accompanying figures, it may be appreciated that other types of displacement sensors may be provided. For instance, the sensor may provide for the absolute or relative measurement of the position of the distal end 1022 of the displacement sensing arm 1010 to provide a displacement measure. For instance, in another embodiment, an optical displacement sensor may be provided. Other types of displacement sensors are also contemplated such as, for example, a capacitive displacement sensor, ultrasonic sensors, Hall effect sensors, or any other sensors known in the art capable of outputting an absolute or relative position measure.

In an embodiment, the coil 1020 may define a passage 1026 extending at least partially through the housing 706. Specifically, the passage 1026 may extend from a proximal face 1028 of the housing 706 to the distal face 1016 of the housing 706. That is, the passage 1026 may extend entirely though the housing 706. An end cap 1030 may be provided that is operable to close the proximal end of the passage 1026 at the proximal face 1028 of the drill housing 706. Furthermore, a biasing member 1032 (e.g., a coil spring) may be provided in the passageway 1026 at a proximal end thereof. The biasing member 1032 may be provided between the end cap 1030 and the proximal end 1022 of the displacement sensing arm 1010. In this regard, the biasing member 1032 may act on the proximal end 1022 of the displacement sensing arm 1010 to bias the displacement sensing arm 1010 distally relative to the passage 1026 and drill housing 706.

As such, the displacement sensing arm 1010 may include features that selectively prevent ejection of the displacement sensing arm 1010 from the distal end of the passage 1026. For example, the displacement sensing arm 1010 may include at least one flat 1034 that extends along a portion of the arm 1010. At the proximal and distal extents of the flat 1034, the displacement sensing arm 1010 may include shoulders 1036 that project from the flats 1034 (best seen at the distal portion 1018 in FIG. 16B and at the proximal portion 1022 in FIG. 17). As such, at the proximal opening of the passage 1026, a selectively displaceable stop 1038 may be disposed relative to the flat 1034 such that the flat 1034 may move relative to the stop 1038, but interfere with the shoulder 1036 defined in the displacement sensing arm 1010 to prevent passage of the shoulder 1036 beyond the stop 1038. In this regard, the length of the displacement sensing arm 1010 along which the flat 1034 extends may be moveable relative to the stop 1038, and the stop 1038 may limit proximal and distal movement of the displacement sensing arm 1010 beyond the stop 1038.

However, the stop 1038 may be displaceable upon depressing, for example, a button 1040 provided on an exterior of the housing 706. Thus, upon depressing the button 1040, the stop 1038 may be displaced away from the displacement sensing arm 1010 to allow the shoulder 1036 to pass distally from the distal end of the passage 1026 such that the displacement sensing arm 1010 may be removed entirely from the passage 1026. The distal end of the flats 1038 may include a detent 1042 that may be engageable with the stop 1038 so as to maintain the displacement sensing arm 1010 in a proximally disposed, retracted position relative to the housing (e.g., as shown in FIG. 17). Once the button 1040 is depressed and released, the detent 1042 at the proximal end of the flat 1034 of the displacement sensing arm 1010 may be released by the stop 1038 and the displacement sensing arm 1010 may move proximally (e.g., under influence of the biasing member 1032). The displacement sensing arm 1010 may move proximally until the shoulder 1036 at the distal end of the flat 1034 are engaged to prevent further distal movement of the displacement sensing arm 1010. Accordingly, the displacement sensing arm 1010 may be retained in a retracted position, released to be moveable relative to and biased proximally with respect to the housing 706, and removable altogether from the housing 706.

In the latter regard, removal of the displacement sensing arm 1010 and biasing member 1032 from the passage 1026 may allow for separate cleaning of those members. Additionally, removal of the end cap 1030 may allow for a cleaning apparatus to be passed through the full length of the passage 1026 to facilitate cleaning thereof.

As referenced above, the distal portion 1018 of the displacement sensing arm 1010 may be adapted to engage a drill bit assembly 1004 that is correspondingly adapted for use with the drill 1002. For instance, as shown in FIGS. 16A-16C and FIG. 17, the displacement sensing arm 1010 may generally be linear along the proximal portion 1022 of the displacement sensing arm 1010. In this regard, the proximal portion 1022 may be adapted to be collinear with the passage 1026 and moveable within the passage 1026. Furthermore, the distal portion 1018 of the displacement sensing arm 1010 (e.g., the portion distal to the linear portion of the displacement sensing arm 1010) may extend from the linear portion of the displacement sensing arm 1010 toward the drill bit assembly 1004 that may be engaged by the chuck 1014 of the drill 1002. In this regard, the linear portion of the displacement sensing arm 1010 may be substantially parallel to and offset from the axis of rotation 726. The distal portion 1018 may extend from the linear portion in a direction corresponding with the offset such that the distal portion 10184 extends toward the drill bit assembly 1004. This may facilitate engagement between the displacement sensing arm 1010 and the bushing 1006 of the drill bit assembly 1004. As shown, in FIGS. 16A-16C and 17, the distal portion 1018 may be an at least partially arcuate member extending along a radius of curvature toward the drill bit assembly 1004. However, the distal portion 1018 may be shaped differently (e.g., the distal portion 1018 may be a linear portion extending at an angle or perpendicularly from the proximal 1022 toward the drill bit assembly 1004).

Figure 18:
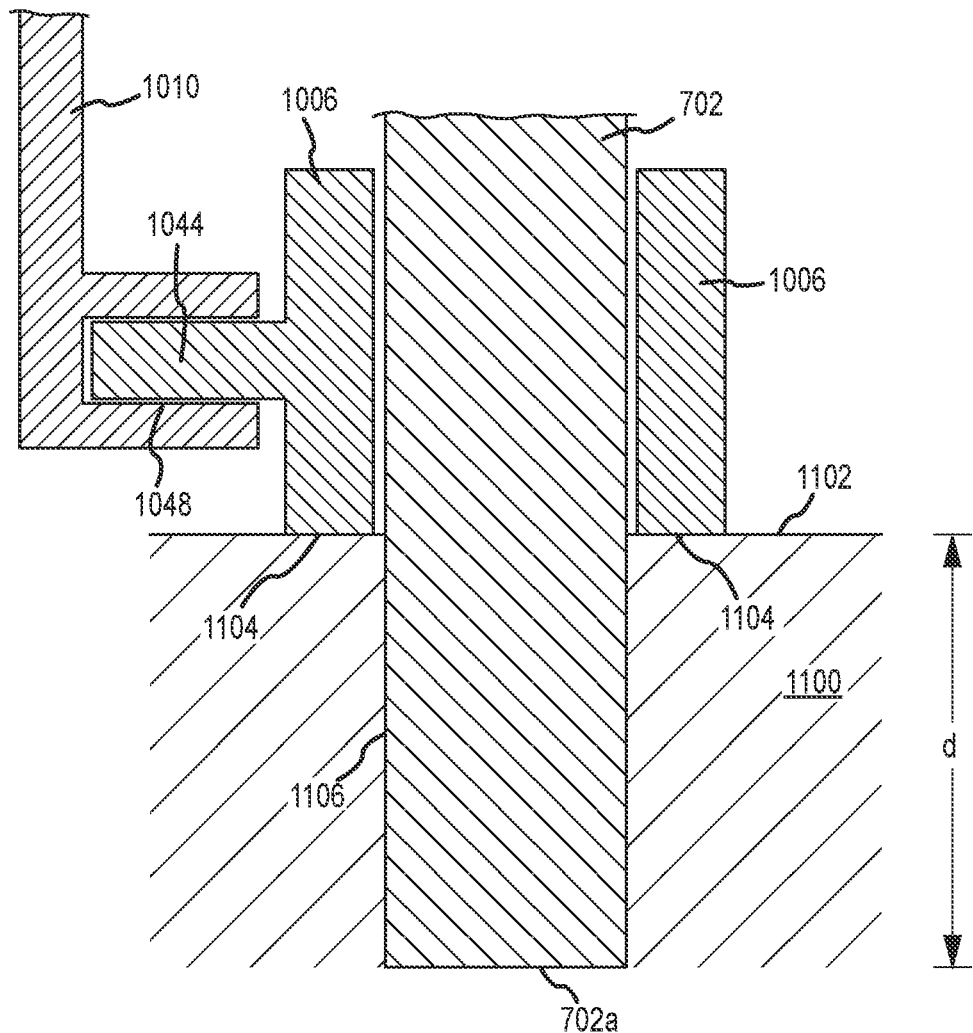
FIG. 18 is a cross sectional schematic view of a drill bit that has been advanced into a bore in a medium relative to a bushing engaged with a distal portion of a displacement sensing arm.

For instance, with further reference to FIG. 18, a schematic section view of a drill bit 702 that has been advanced into a medium 1100 is shown. The bushing 1006 may be disposed about the drill bit 702. As such, the bushing 1006 may be disposed about the periphery of a bore 1102 created upon advancement of the drill bit 702 into the medium 1100. That is, the bushing 1006 may remain in contact with the surface 1102 of the medium 1100 upon advancement of the drill bit 702 into the medium 1100. In this regard, the bushing 1006 may include a reference surface 1104 at a distal portion thereof. The reference surface 1104 may contact the surface 1102 of the medium 1100 to be drilled. As such, prior to initiation of the drilling when the leading edge 702a of the drill bit 702 is also in contact with the surface 1102, the displacement sensor 1008 may be set to establish the reference point. Accordingly, as the drill bit 702 is advanced, the reference surface 1104 may remain in contact with the surface 1102 of the medium 1100. The reference surface 1104 may contact the surface 1102 about a periphery of a bore 1106. In an embodiment, the reference surface 1104 may extend circumferentially about a majority or substantially all of the drill bit 702 such that the reference surface 1104 may also extend circumferentially about a majority of or substantially all of the periphery of the bore 1106. The distally biased displacement sensing arm 1010 may act on the bushing 1006 (e.g., by way of post 1044 received in hole 1048) to maintain the bushing 1006 in contact with the surface 1102. In any regard, the displacement (d) of the leading edge 702a of the drill bit 702 relative to the reference surface 1104 of the bushing 1006 may be measured upon corresponding movement of the core 1024 at the proximal end 1022 of the displacement sensing arm 1010 relative to the coil 1020.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A system for monitoring use of a working tool with a powered surgical instrument, the system comprising:
   a powered surgical instrument comprising a drive motor;
   a working tool that is removably engageable with the powered instrument, wherein the powered instrument is operable to drive the working tool when the working tool is engaged with the powered instrument to accomplish an operation, and wherein the working tool includes an identifier;
   a reader associated with the powered instrument and operative to read the identifier of the working tool when the working tool is engaged with the powered instrument;
   a controller in operative communication with the reader that is operative to receive information regarding the identifier and associate the working tool with the powered instrument; and
   a sensor configured to measure at least one characteristic associated with the operation of the working tool, wherein the controller is configured to receive the at least one characteristic associated with the operation of the working tool, and wherein the controller is operative to process the information regarding the identifier and the at least one characteristic associated with the operation of the working tool to provide an output.

2. The system as set forth in claim 1, wherein the working tool comprises a connection portion for selective engagement of the working tool with the powered instrument, and the unique identifier is adjacent the connector portion of the working tool.

3. The system as set forth in claim 2, wherein the powered instrument comprises an engagement portion that engages the connection portion of the working tool and the reader is adjacent to the engagement portion such that the unique identifier is readable by the reader when the working tool is engaged by the engagement portion of the powered instrument.

4. The system as set forth in claim 1, wherein the controller is operable to generate the output responsive to receipt of the information regarding the unique identifier.

5. The system as set forth in claim 4, wherein the receipt of the information regarding the unique identifier is indicative of engagement of the working tool with the powered instrument.

6. The system as set forth in claim 5, wherein the controller is operative to control the drive motor, and wherein the controller disables the drive motor until and unless the information regarding the unique identifier is received.

7. The system as set forth in claim 1, wherein the unique identifier is indicative of a working tool attribute.

8. The system as set forth in claim 7, wherein the working tool attribute comprises at least one of a working tool size, a working tool material, a working tool weight, a working tool manufacturer, and a working tool serial number.

9. The system as set forth in claim 1, wherein the sensor is configured to measure the displacement of the working tool relative to an axis along which the working tool is advanced during the operation.

10. The system as set forth in claim 7, wherein the controller is operative to determine an instrument operating condition and is operative to provide the output responsive to the determination of the instrument operating condition.

11. The system as set forth in claim 10, wherein the instrument operating condition is at least partially based on the working tool attribute.

12. The system as set forth in claim 11, wherein the instrument operating condition is indicative of a condition-dependent status, the condition-dependent status corresponding to a physical condition of the instrument.

13. The system as set forth in claim 12, wherein the working tool is one of a plurality of working tools, each of the plurality of working tools being removably engageable with the powered surgical instrument, and wherein the powered surgical instrument operating condition is indicative of an inventory-dependent status, the inventory-dependent status corresponding to engagement of a subset of the plurality of working tools with the instrument.

14. The system as set forth in claim 10, further comprising:
a collection module that is configured to associate the instrument operating condition with a health history characteristic of a subject of a surgical operation, the health history characteristic comprising at least one of age, weight, sex, nationality, geographic location, medication history, and disease history.

15. The system as set forth in claim 1, wherein the controller is remotely disposed from the instrument, and wherein the instrument further comprises:
a transmitter for transmitting a communications signal to the controller, the communications signal indicative of the information regarding the unique identifier.

16. The system as set forth in claim 1, wherein the unique identifier comprises a radio frequency identification (RFID) tag.

17. The system as set forth in claim 16, wherein the reader includes a radio frequency identification (RFID) reader.

* * * * *